United States Patent
Burton et al.

(10) Patent No.: US 12,392,642 B2
(45) Date of Patent: *Aug. 19, 2025

(54) METHODS, SYSTEMS AND DEVICES FOR GENERATING REAL-TIME ACTIVITY DATA UPDATES TO DISPLAY DEVICES

(71) Applicant: Fitbit, Inc., San Francisco, CA (US)

(72) Inventors: Barry Burton, San Francisco, CA (US); Heiko Panther, Oakland, CA (US); James Park, Berkeley, CA (US); Eric Friedman, San Francisco, CA (US); Shelten Yuen, Berkeley, CA (US); Christine Brumback, San Francisco, CA (US); Timothy Roberts, San Francisco, CA (US)

(73) Assignee: FITBIT, INC., San Francisco, CA (US)

( * ) Notice: Subject to any disclaimer, the term of this patent is extended or adjusted under 35 U.S.C. 154(b) by 496 days.

This patent is subject to a terminal disclaimer.

(21) Appl. No.: 17/666,112

(22) Filed: Feb. 7, 2022

(65) Prior Publication Data
US 2022/0260389 A1 Aug. 18, 2022

Related U.S. Application Data

(60) Continuation of application No. 14/938,704, filed on Nov. 11, 2015, now Pat. No. 11,243,093, which is a
(Continued)

(51) Int. Cl.
*G01C 22/00* (2006.01)
*A61B 5/00* (2006.01)
(Continued)

(52) U.S. Cl.
CPC .......... *G01C 22/006* (2013.01); *A61B 5/0002* (2013.01); *A61B 5/1118* (2013.01);
(Continued)

(58) Field of Classification Search
CPC ............... G01C 22/006; G06F 19/3406; G06F 19/3481; H04L 67/22; H04W 4/008
See application file for complete search history.

(56) References Cited

U.S. PATENT DOCUMENTS

| | | |
|---|---|---|
| 2,284,849 A | 8/1941 | Anderson et al. |
| 2,717,736 A | 9/1955 | Schlesinger |

(Continued)

FOREIGN PATENT DOCUMENTS

| | | |
|---|---|---|
| CN | 101789933 | 7/2010 |
| CN | 101978374 | 2/2011 |

(Continued)

OTHER PUBLICATIONS

"Activator is One of the Best Cydia iPhone Hacks I Control your iPhone with Gestures," iphone-tips-and-advice.com, [retrieved on Jul. 9, 2013 at http://www.iphone-tips-andadvice.comlactivatior. html], 10 pp.

(Continued)

*Primary Examiner* — Omer S Khan
(74) *Attorney, Agent, or Firm* — DORITY & MANNING P.A.

(57) ABSTRACT

Methods, systems and devices are provided for displaying monitored activity data in substantial real-time on a screen of a computing device. One example method includes capturing motion data associated with activity of a user via an activity tracking device. The motion data is quantified into a plurality of metrics associated with the activity of the user. The method includes connecting the activity tracking device with a computing device over a wireless data connection, and sending motion data from the activity tracking device to the computing device for display of one or more of the plurality of metrics on a graphical user interface of the computing device. At least one of the plurality of metrics (Continued)

displayed on the graphical user interface is shown to change in substantial real-time based on the motion data.

12 Claims, 13 Drawing Sheets

Related U.S. Application Data continuation of application No. 14/050,301, filed on Oct. 9, 2013, now Pat. No. 9,188,460, which is a continuation-in-part of application No. 13/959,714, filed on Aug. 5, 2013, now Pat. No. 8,762,101, which is a continuation-in-part of application No. 13/759,485, filed on Feb. 5, 2013, now Pat. No. 8,543,351, and a continuation-in-part of application No. 13/693,334, filed on Dec. 4, 2012, now Pat. No. 8,548,770, which is a division of application No. 13/667,229, filed on Nov. 2, 2012, now Pat. No. 8,437,980, said application No. 13/759,485 is a division of application No. 13/667,229, filed on Nov. 2, 2012, now Pat. No. 8,437,980, which is a division of application No. 13/469,027, filed on May 10, 2012, now Pat. No. 8,311,769, which is a division of application No. 13/246,843, filed on Sep. 27, 2011, now Pat. No. 8,180,591, which is a division of application No. 13/156,304, filed on Jun. 8, 2011, now Pat. No. 9,167,991.

(60) Provisional application No. 61/885,966, filed on Oct. 2, 2013, provisional application No. 61/390,811, filed on Oct. 7, 2010, provisional application No. 61/388,595, filed on Sep. 30, 2010.

(51) Int. Cl.
*A61B 5/11* (2006.01)
*A61B 5/22* (2006.01)
*G16H 40/67* (2018.01)
*H04L 67/50* (2022.01)
*H04W 4/80* (2018.01)
*A61B 5/0205* (2006.01)
*A61B 5/024* (2006.01)
*G16H 40/63* (2018.01)

(52) U.S. Cl.
CPC ............ *A61B 5/222* (2013.01); *G16H 40/67* (2018.01); *H04L 67/535* (2022.05); *H04W 4/80* (2018.02); *A61B 5/02055* (2013.01); *A61B 5/02438* (2013.01); *A61B 5/1112* (2013.01); *A61B 5/1123* (2013.01); *A61B 5/4812* (2013.01); *A61B 5/4815* (2013.01); *A61B 5/4866* (2013.01); *A61B 5/681* (2013.01); *A61B 5/6838* (2013.01); *A61B 5/7264* (2013.01); *A61B 2560/0214* (2013.01); *A61B 2560/0242* (2013.01); *A61B 2560/0456* (2013.01); *A61B 2562/0219* (2013.01); *G16H 40/63* (2018.01)

(56) References Cited

U.S. PATENT DOCUMENTS

| | | |
|---|---|---|
| 2,827,309 A | 3/1958 | Fred |
| 2,883,255 A | 4/1959 | Anderson |
| 3,163,856 A | 12/1964 | Kirby |
| 3,250,270 A | 5/1966 | Walter |
| 3,522,383 A | 7/1970 | Chang |
| 3,918,658 A | 11/1975 | Beller |
| 4,192,000 A | 3/1980 | Lipsey |
| 4,244,020 A | 1/1981 | Ratcliff |
| 4,281,663 A | 8/1981 | Pringle |
| 4,284,849 A | 8/1981 | Anderson et al. |
| 4,312,358 A | 1/1982 | Barney |
| 4,367,752 A | 1/1983 | Jimenez et al. |
| 4,390,922 A | 6/1983 | Pelliccia |
| 4,407,295 A | 10/1983 | Steuer et al. |
| 4,425,921 A | 1/1984 | Fujisaki et al. |
| 4,466,204 A | 8/1984 | Wu |
| 4,575,804 A | 3/1986 | Ratcliff |
| 4,578,769 A | 3/1986 | Frederick |
| 4,617,525 A | 10/1986 | Lloyd |
| 4,887,249 A | 12/1989 | Thinesen |
| 4,930,518 A | 6/1990 | Hrushesky |
| 4,977,509 A | 12/1990 | Pitchford et al. |
| 5,058,427 A | 10/1991 | Brandt |
| 5,224,059 A | 6/1993 | Nitta et al. |
| 5,295,085 A | 3/1994 | Hoffacker |
| 5,314,389 A | 5/1994 | Dotan |
| 5,323,650 A | 6/1994 | Fullen et al. |
| 5,365,930 A | 11/1994 | Takashima et al. |
| 5,446,705 A | 8/1995 | Haas et al. |
| 5,456,648 A | 10/1995 | Edinburg et al. |
| 5,553,296 A | 9/1996 | Forrest et al. |
| 5,583,776 A | 12/1996 | Levi et al. |
| 5,645,509 A | 7/1997 | Brewer et al. |
| 5,671,162 A | 9/1997 | Werbin |
| 5,692,324 A | 12/1997 | Goldston et al. |
| 5,704,350 A | 1/1998 | Williams, III |
| 5,724,265 A | 3/1998 | Hutchings |
| 5,817,008 A | 10/1998 | Rafert et al. |
| 5,890,128 A | 3/1999 | Diaz et al. |
| 5,891,042 A | 4/1999 | Sham et al. |
| 5,894,454 A | 4/1999 | Kondo |
| 5,899,963 A | 5/1999 | Hutchings |
| 5,941,828 A | 8/1999 | Archibald et al. |
| 5,947,868 A | 9/1999 | Dugan |
| 5,955,667 A | 9/1999 | Fyfe |
| 5,976,083 A | 11/1999 | Richardson et al. |
| 6,018,705 A | 1/2000 | Gaudet et al. |
| 6,077,193 A | 6/2000 | Buhler et al. |
| 6,078,874 A | 6/2000 | Piety et al. |
| 6,085,248 A | 7/2000 | Sambamurthy et al. |
| 6,129,686 A | 10/2000 | Friedman |
| 6,145,389 A | 11/2000 | Ebeling et al. |
| 6,183,425 B1 | 2/2001 | Whalen et al. |
| 6,213,872 B1 | 4/2001 | Harada et al. |
| 6,241,684 B1 | 6/2001 | Amano et al. |
| 6,287,262 B1 | 9/2001 | Amano et al. |
| 6,301,964 B1 | 10/2001 | Fyfe et al. |
| 6,302,789 B2 | 10/2001 | Harada et al. |
| 6,305,221 B1 | 10/2001 | Hutchings |
| 6,309,360 B1 | 10/2001 | Mault |
| 6,454,708 B1 | 9/2002 | Ferguson et al. |
| 6,469,639 B2 | 10/2002 | Tanenhaus et al. |
| 6,478,736 B1 | 11/2002 | Mault |
| 6,513,381 B2 | 2/2003 | Fyfe et al. |
| 6,513,532 B2 | 2/2003 | Mault et al. |
| 6,527,711 B1 | 3/2003 | Stivoric et al. |
| 6,529,827 B1 | 3/2003 | Beason et al. |
| 6,558,335 B1 | 5/2003 | Thede |
| 6,561,951 B2 | 5/2003 | Cannon et al. |
| 6,571,200 B1 | 5/2003 | Mault |
| 6,583,369 B2 | 6/2003 | Montagnino et al. |
| 6,585,622 B1 | 7/2003 | Shum et al. |
| 6,607,493 B2 | 8/2003 | Song |
| 6,620,078 B2 | 9/2003 | Pfeffer |
| 6,678,629 B2 | 1/2004 | Tsuji |
| 6,699,188 B2 | 3/2004 | Wessel |
| 6,761,064 B2 | 7/2004 | Tsuii |
| 6,772,331 B1 | 8/2004 | Hind et al. |
| 6,788,200 B1 | 9/2004 | Jamel et al. |
| 6,790,178 B1 | 9/2004 | Mault et al. |
| 6,808,473 B2 | 10/2004 | Hisano et al. |
| 6,811,516 B1 | 11/2004 | Dugan |
| 6,813,582 B2 | 11/2004 | Levi et al. |
| 6,813,931 B2 | 11/2004 | Yaday et al. |
| 6,856,938 B2 | 2/2005 | Kurtz |
| 6,862,575 B1 | 3/2005 | Anttila et al. |

(56) References Cited

U.S. PATENT DOCUMENTS

| | | |
|---|---|---|
| 6,984,207 B1 | 1/2006 | Sullivan et al. |
| 7,020,508 B2 | 3/2006 | Stivoric et al. |
| 7,041,032 B1 | 5/2006 | Calvano |
| 7,062,225 B2 | 6/2006 | White |
| 7,099,237 B2 | 8/2006 | Lall |
| 7,133,690 B2 | 11/2006 | Ranta-Aho et al. |
| 7,162,368 B2 | 1/2007 | Levi et al. |
| 7,171,331 B2 | 1/2007 | Vock et al. |
| 7,200,517 B2 | 4/2007 | Darley et al. |
| 7,246,033 B1 | 7/2007 | Kudo |
| 7,261,690 B2 | 8/2007 | Teller et al. |
| 7,272,982 B2 | 9/2007 | Neuhauser et al. |
| 7,283,870 B2 | 10/2007 | Kaiser et al. |
| 7,285,090 B2 | 10/2007 | Stivoric et al. |
| 7,373,820 B1 | 5/2008 | James |
| 7,443,292 B2 | 10/2008 | Jensen et al. |
| 7,457,724 B2 | 11/2008 | Vock et al. |
| 7,467,060 B2 | 12/2008 | Kulach et al. |
| 7,499,439 B2 * | 3/2009 | Li ................. H04L 47/25 370/335 |
| 7,502,643 B2 | 3/2009 | Farringdon et al. |
| 7,505,865 B2 | 3/2009 | Ohkubo et al. |
| 7,539,532 B2 | 5/2009 | Tran |
| 7,558,622 B2 | 7/2009 | Tran |
| 7,559,877 B2 | 7/2009 | Parks et al. |
| 7,608,050 B2 | 10/2009 | Shuoo |
| 7,653,508 B1 | 1/2010 | Kahn et al. |
| 7,690,556 B1 | 4/2010 | Kahn et al. |
| 7,713,173 B2 | 5/2010 | Shin et al. |
| 7,762,952 B2 | 7/2010 | Lee et al. |
| 7,771,320 B2 | 8/2010 | Riley et al. |
| 7,774,156 B2 | 8/2010 | Niva et al. |
| 7,789,802 B2 | 9/2010 | Lee et al. |
| 7,827,000 B2 | 11/2010 | Stirling et al. |
| 7,865,140 B2 | 1/2011 | Levien et al. |
| 7,881,902 B1 | 2/2011 | Kahn et al. |
| 7,907,901 B1 | 3/2011 | Kahn et al. |
| 7,925,022 B2 | 4/2011 | Jung et al. |
| 7,927,253 B2 | 4/2011 | Vincent et al. |
| 7,941,665 B2 | 5/2011 | Berkema et al. |
| 7,942,824 B1 | 5/2011 | Kayyali et al. |
| 7,953,549 B2 | 5/2011 | Graham et al. |
| 7,983,876 B2 | 7/2011 | Vock et al. |
| 8,005,922 B2 | 8/2011 | Boudreau et al. |
| 8,028,443 B2 | 10/2011 | Case, Jr. |
| 8,036,850 B2 | 10/2011 | Kulach et al. |
| 8,055,469 B2 | 11/2011 | Kulach et al. |
| 8,059,573 B2 | 11/2011 | Julian et al. |
| 8,060,337 B2 | 11/2011 | Kulach et al. |
| 8,095,071 B2 | 1/2012 | Sim et al. |
| 8,099,318 B2 | 1/2012 | Moukas et al. |
| 8,103,247 B2 | 1/2012 | Ananthanarayanan et al. |
| 8,132,037 B2 | 3/2012 | Fehr et al. |
| 8,172,761 B1 | 5/2012 | Rulkov et al. |
| 8,177,260 B2 | 5/2012 | Trooper et al. |
| 8,180,591 B2 | 5/2012 | Yuen et al. |
| 8,180,592 B2 | 5/2012 | Yuen et al. |
| 8,190,651 B2 | 5/2012 | Treu et al. |
| 8,213,613 B2 | 7/2012 | Diehl et al. |
| 8,260,261 B2 | 9/2012 | Teague |
| 8,270,297 B2 | 9/2012 | Akasaka et al. |
| 8,271,662 B1 | 9/2012 | Gossweiler, III et al. |
| 8,289,162 B2 | 10/2012 | Mooring et al. |
| 8,311,769 B2 | 11/2012 | Yuen et al. |
| 8,311,770 B2 | 11/2012 | Yuen et al. |
| 8,386,008 B2 | 2/2013 | Yuen et al. |
| 8,437,980 B2 | 5/2013 | Yuen et al. |
| 8,462,591 B1 | 6/2013 | Marhaben |
| 8,463,576 B2 | 6/2013 | Yuen et al. |
| 8,463,577 B2 | 6/2013 | Yuen et al. |
| 8,487,771 B2 | 7/2013 | Hsieh et al. |
| 8,533,269 B2 | 9/2013 | Brown |
| 8,533,620 B2 | 9/2013 | Hoffman et al. |
| 8,543,185 B2 | 9/2013 | Yuen et al. |
| 8,543,351 B2 | 9/2013 | Yuen et al. |
| 8,548,770 B2 | 10/2013 | Yuen et al. |
| 8,562,489 B2 | 10/2013 | Burton et al. |
| 8,583,402 B2 | 11/2013 | Yuen et al. |
| 8,597,093 B2 | 12/2013 | Engelberg et al. |
| 8,634,796 B2 | 1/2014 | Johnson |
| 8,638,228 B2 | 1/2014 | Amico et al. |
| 8,670,953 B2 | 3/2014 | Yuen et al. |
| 8,684,900 B2 | 4/2014 | Tran |
| 8,690,578 B1 | 4/2014 | Nusbaum et al. |
| 8,738,321 B2 | 5/2014 | Yuen et al. |
| 8,738,323 B2 | 5/2014 | Yuen et al. |
| 8,744,803 B2 | 6/2014 | Park et al. |
| 8,762,101 B2 | 6/2014 | Yuen et al. |
| 8,764,651 B2 | 7/2014 | Tran |
| 8,825,445 B2 | 9/2014 | Hoffman et al. |
| 8,847,988 B2 | 9/2014 | Geisner et al. |
| 8,868,377 B2 | 10/2014 | Yuen et al. |
| 8,892,401 B2 | 11/2014 | Yuen et al. |
| 8,949,070 B1 | 2/2015 | Kahn et al. |
| 8,954,135 B2 | 2/2015 | Yuen et al. |
| 8,954,289 B2 | 2/2015 | Burton et al. |
| 8,954,290 B2 | 2/2015 | Yuen et al. |
| 8,961,414 B2 | 2/2015 | Teller et al. |
| 8,968,195 B2 | 3/2015 | Tran |
| 9,047,648 B1 | 6/2015 | Lekutai et al. |
| 9,081,534 B2 | 7/2015 | Yuen et al. |
| 9,113,823 B2 | 8/2015 | Yuen et al. |
| 9,137,849 B1 | 9/2015 | Wright |
| 9,183,738 B1 | 11/2015 | Allen, Sr. et al. |
| 9,188,460 B2 | 11/2015 | Burton et al. |
| 9,374,279 B2 | 6/2016 | Yuen et al. |
| 9,426,769 B2 | 8/2016 | Haro |
| 9,641,239 B2 | 5/2017 | Panther et al. |
| 10,218,433 B2 | 2/2019 | Panther et al. |
| 10,700,774 B2 | 6/2020 | Panther et al. |
| 2001/0049470 A1 | 12/2001 | Mault et al. |
| 2001/0055242 A1 | 12/2001 | Deshmuhk et al. |
| 2002/0013717 A1 | 1/2002 | Ando et al. |
| 2002/0019585 A1 | 2/2002 | Dickenson |
| 2002/0077219 A1 | 6/2002 | Cohen et al. |
| 2002/0082144 A1 | 6/2002 | Pfeffer |
| 2002/0087264 A1 | 7/2002 | Hills et al. |
| 2002/0109600 A1 | 8/2002 | Mault et al. |
| 2002/0178060 A1 | 11/2002 | Sheehan |
| 2002/0191797 A1 | 12/2002 | Perlman |
| 2002/0198776 A1 | 12/2002 | Nara et al. |
| 2003/0018523 A1 | 1/2003 | Rappaport et al. |
| 2003/0050537 A1 | 3/2003 | Wessel |
| 2003/0065561 A1 | 4/2003 | Brown et al. |
| 2003/0107575 A1 | 6/2003 | Cardno |
| 2003/0131059 A1 | 7/2003 | Brown et al. |
| 2003/0171189 A1 | 9/2003 | Kaufman |
| 2003/0208335 A1 | 11/2003 | Unuma et al. |
| 2003/0226695 A1 | 12/2003 | Mault |
| 2004/0054497 A1 | 3/2004 | Kurtz |
| 2004/0061324 A1 | 4/2004 | Howard |
| 2004/0117963 A1 | 6/2004 | Schneider |
| 2004/0122488 A1 | 6/2004 | Mazar et al. |
| 2004/0152957 A1 | 8/2004 | Stivoric et al. |
| 2004/0192322 A1 * | 9/2004 | Dacosta ............... H04W 28/20 455/451 |
| 2004/0239497 A1 | 12/2004 | Schwartzman et al. |
| 2004/0249299 A1 | 12/2004 | Cobb |
| 2004/0257557 A1 | 12/2004 | Block |
| 2005/0037844 A1 | 2/2005 | Shum et al. |
| 2005/0038679 A1 | 2/2005 | Short |
| 2005/0054938 A1 | 3/2005 | Wehman et al. |
| 2005/0102172 A1 | 5/2005 | Sirmans, Jr. |
| 2005/0107723 A1 | 5/2005 | Wehman et al. |
| 2005/0163056 A1 | 7/2005 | Ranta-Aho et al. |
| 2005/0171410 A1 | 8/2005 | Hielt et al. |
| 2005/0186965 A1 | 8/2005 | Pagonis et al. |
| 2005/0187481 A1 | 8/2005 | Hatib |
| 2005/0195830 A1 | 9/2005 | Chitrapu et al. |
| 2005/0216724 A1 | 9/2005 | Isozaki et al. |
| 2005/0228244 A1 | 10/2005 | Banet |
| 2005/0228692 A1 | 10/2005 | Hodgdon |
| 2005/0234742 A1 | 10/2005 | Hodgdon |
| 2005/0248718 A1 | 11/2005 | Howell et al. |

(56) References Cited

U.S. PATENT DOCUMENTS

| | | |
|---|---|---|
| 2005/0272564 A1 | 12/2005 | Pvles et al. |
| 2006/0004265 A1 | 1/2006 | Pulkkinen et al. |
| 2006/0020174 A1 | 1/2006 | Matsumura |
| 2006/0020177 A1 | 1/2006 | Seo et al. |
| 2006/0025282 A1 | 2/2006 | Redmann |
| 2006/0039348 A1 | 2/2006 | Racz et al. |
| 2006/0047208 A1 | 3/2006 | Yoon |
| 2006/0047447 A1 | 3/2006 | Brady et al. |
| 2006/0064037 A1 | 3/2006 | Shalon et al. |
| 2006/0064276 A1 | 3/2006 | Ren et al. |
| 2006/0069619 A1 | 3/2006 | Walker et al. |
| 2006/0089542 A1 | 4/2006 | Sands |
| 2006/0106535 A1 | 5/2006 | Duncan |
| 2006/0111944 A1 | 5/2006 | Sirmans, Jr. |
| 2006/0129436 A1 | 6/2006 | Short |
| 2006/0143645 A1 | 6/2006 | Vock et al. |
| 2006/0166718 A1 | 7/2006 | Seshadri et al. |
| 2006/0189863 A1 | 8/2006 | Peyser |
| 2006/0217231 A1 | 9/2006 | Parks et al. |
| 2006/0247952 A1 | 11/2006 | Muraca |
| 2006/0277474 A1 | 12/2006 | Robarts et al. |
| 2006/0282021 A1 | 12/2006 | Devaul et al. |
| 2006/0287883 A1 | 12/2006 | Turgiss et al. |
| 2006/0288117 A1 | 12/2006 | Raveendran et al. |
| 2007/0011028 A1 | 1/2007 | Sweenev |
| 2007/0049384 A1 | 3/2007 | King et al. |
| 2007/0050715 A1 | 3/2007 | Behar |
| 2007/0051369 A1 | 3/2007 | Choi et al. |
| 2007/0061593 A1 | 3/2007 | Celikkan et al. |
| 2007/0071643 A1 | 3/2007 | Hall et al. |
| 2007/0072156 A1 | 3/2007 | Kaufman et al. |
| 2007/0083095 A1 | 4/2007 | Rippe et al. |
| 2007/0083602 A1 | 4/2007 | Heaaenhougen et al. |
| 2007/0123391 A1 | 5/2007 | Shin et al. |
| 2007/0135264 A1 | 6/2007 | Rosenberg |
| 2007/0136093 A1 | 6/2007 | Rankin et al. |
| 2007/0146116 A1 | 6/2007 | Kimbrell |
| 2007/0150929 A1* | 6/2007 | Kizaki ........... H04N 21/440281 725/132 |
| 2007/0155277 A1 | 7/2007 | Amitai et al. |
| 2007/0159926 A1 | 7/2007 | Prstojevich et al. |
| 2007/0179356 A1 | 8/2007 | Wessel |
| 2007/0179761 A1 | 8/2007 | Wren et al. |
| 2007/0194066 A1 | 8/2007 | Ishihara et al. |
| 2007/0197920 A1 | 8/2007 | Adams |
| 2007/0208544 A1 | 9/2007 | Kulach et al. |
| 2007/0276271 A1 | 11/2007 | Chan |
| 2007/0288265 A1 | 12/2007 | Quinian et al. |
| 2008/0001735 A1 | 1/2008 | Tran |
| 2008/0014947 A1 | 1/2008 | Carnall |
| 2008/0022089 A1 | 1/2008 | Leedom |
| 2008/0032864 A1 | 2/2008 | Hakki |
| 2008/0044014 A1 | 2/2008 | Corndorf |
| 2008/0054072 A1 | 3/2008 | Katraaadda et al. |
| 2008/0084823 A1 | 4/2008 | Akasaka et al. |
| 2008/0093838 A1 | 4/2008 | Tropper et al. |
| 2008/0097550 A1 | 4/2008 | Dicks et al. |
| 2008/0109158 A1 | 5/2008 | Huhtala |
| 2008/0114829 A1 | 5/2008 | Button et al. |
| 2008/0125288 A1 | 5/2008 | Case |
| 2008/0125959 A1 | 5/2008 | Doherty |
| 2008/0129457 A1 | 6/2008 | Ritter et al. |
| 2008/0134102 A1 | 6/2008 | Movold et al. |
| 2008/0139910 A1 | 6/2008 | Mastrototaro et al. |
| 2008/0140163 A1 | 6/2008 | Keacher et al. |
| 2008/0140338 A1 | 6/2008 | No et al. |
| 2008/0146892 A1 | 6/2008 | LeBoeuf et al. |
| 2008/0155077 A1 | 6/2008 | James |
| 2008/0176655 A1 | 7/2008 | James et al. |
| 2008/0190202 A1 | 8/2008 | Kulach et al. |
| 2008/0214360 A1 | 9/2008 | Stirling et al. |
| 2008/0275309 A1 | 11/2008 | Stivoric et al. |
| 2008/0285805 A1 | 11/2008 | Luinge et al. |
| 2008/0287751 A1 | 11/2008 | Stivoric et al. |
| 2008/0300641 A1 | 12/2008 | Brunekreeft |
| 2009/0012418 A1 | 1/2009 | Gerlach |
| 2009/0018797 A1 | 1/2009 | Kasama et al. |
| 2009/0043531 A1 | 2/2009 | Kahn et al. |
| 2009/0047645 A1 | 2/2009 | Dibenedetto et al. |
| 2009/0048044 A1 | 2/2009 | Oleson et al. |
| 2009/0048070 A1* | 2/2009 | Vincent .................. A61B 5/112 482/8 |
| 2009/0054737 A1 | 2/2009 | Magar et al. |
| 2009/0054751 A1 | 2/2009 | Babashan et al. |
| 2009/0058635 A1 | 3/2009 | Lalonde et al. |
| 2009/0063193 A1 | 3/2009 | Barton et al. |
| 2009/0063293 A1 | 3/2009 | Mirrashidi et al. |
| 2009/0076765 A1 | 3/2009 | Kulach et al. |
| 2009/0088183 A1 | 4/2009 | Piersol |
| 2009/0093341 A1 | 4/2009 | James et al. |
| 2009/0098821 A1 | 4/2009 | Shinya |
| 2009/0144456 A1 | 6/2009 | Gelf et al. |
| 2009/0144639 A1 | 6/2009 | Nims et al. |
| 2009/0150178 A1 | 6/2009 | Sutton et al. |
| 2009/0156172 A1 | 6/2009 | Chan |
| 2009/0171788 A1 | 7/2009 | Tropper et al. |
| 2009/0195350 A1 | 8/2009 | Tsern et al. |
| 2009/0262088 A1 | 10/2009 | Moll-Carrillo et al. |
| 2009/0264713 A1 | 10/2009 | Van Loenen et al. |
| 2009/0271147 A1 | 10/2009 | Sugai |
| 2009/0287921 A1 | 11/2009 | Zhu et al. |
| 2009/0307517 A1 | 12/2009 | Fehr et al. |
| 2009/0309742 A1 | 12/2009 | Alexander et al. |
| 2009/0313857 A1 | 12/2009 | Carnes et al. |
| 2010/0023348 A1 | 1/2010 | Hardee et al. |
| 2010/0043056 A1 | 2/2010 | Ganapathy |
| 2010/0058064 A1 | 3/2010 | Kirovski et al. |
| 2010/0059561 A1 | 3/2010 | Ellis et al. |
| 2010/0069203 A1 | 3/2010 | Kawaguchi et al. |
| 2010/0079291 A1 | 4/2010 | Kroll |
| 2010/0120362 A1 | 5/2010 | Walley et al. |
| 2010/0125729 A1 | 5/2010 | Baentsch et al. |
| 2010/0130873 A1 | 5/2010 | Yuen et al. |
| 2010/0158494 A1 | 6/2010 | King |
| 2010/0159709 A1 | 6/2010 | Kotani et al. |
| 2010/0167783 A1 | 7/2010 | Alameh et al. |
| 2010/0179411 A1 | 7/2010 | Holmstrom et al. |
| 2010/0185064 A1 | 7/2010 | Bandic et al. |
| 2010/0191153 A1 | 7/2010 | Sanders et al. |
| 2010/0203833 A1* | 8/2010 | Dorsey ................. G06F 16/437 455/41.2 |
| 2010/0205541 A1 | 8/2010 | Rapaport et al. |
| 2010/0217099 A1 | 8/2010 | LeBouef et al. |
| 2010/0222179 A1 | 9/2010 | Temple et al. |
| 2010/0261987 A1 | 10/2010 | Karnath et al. |
| 2010/0292050 A1 | 11/2010 | DiBenedetto |
| 2010/0292600 A1 | 11/2010 | DiBenedetto et al. |
| 2010/0295684 A1 | 11/2010 | Hsieh et al. |
| 2010/0298656 A1 | 11/2010 | Mccombie et al. |
| 2010/0298661 A1 | 11/2010 | McCombie et al. |
| 2010/0302979 A1 | 12/2010 | Reunamaki |
| 2010/0304674 A1 | 12/2010 | Kim et al. |
| 2010/0311544 A1 | 12/2010 | Robinette et al. |
| 2010/0317289 A1 | 12/2010 | Desai et al. |
| 2010/0331145 A1 | 12/2010 | Lakovic et al. |
| 2011/0003665 A1 | 1/2011 | Burton et al. |
| 2011/0009051 A1 | 1/2011 | Khedouri et al. |
| 2011/0021142 A1 | 1/2011 | Desai et al. |
| 2011/0021143 A1 | 1/2011 | Kapur et al. |
| 2011/0022349 A1 | 1/2011 | Stirling et al. |
| 2011/0029241 A1 | 2/2011 | Miller et al. |
| 2011/0032105 A1 | 2/2011 | Hoffman et al. |
| 2011/0051665 A1 | 3/2011 | Huang |
| 2011/0080349 A1 | 4/2011 | Holbein et al. |
| 2011/0087076 A1 | 4/2011 | Brynelsen et al. |
| 2011/0106449 A1 | 5/2011 | Chowdharv et al. |
| 2011/0109540 A1 | 5/2011 | Milne et al. |
| 2011/0126185 A1 | 5/2011 | Waris et al. |
| 2011/0131005 A1 | 6/2011 | Ueshima et al. |
| 2011/0145894 A1 | 6/2011 | Garcia Morchon et al. |
| 2011/0153773 A1 | 6/2011 | Vandwalle |
| 2011/0167182 A1 | 7/2011 | Palin et al. |
| 2011/0167262 A1 | 7/2011 | Ross et al. |
| 2011/0193704 A1 | 8/2011 | Harper et al. |

(56) References Cited

U.S. PATENT DOCUMENTS

| | | |
|---|---|---|
| 2011/0197157 A1 | 8/2011 | Hoffman et al. |
| 2011/0214030 A1 | 9/2011 | Greenberg et al. |
| 2011/0221590 A1 | 9/2011 | Baker et al. |
| 2011/0224508 A1 | 9/2011 | Moon |
| 2011/0230729 A1 | 9/2011 | Shirasaki et al. |
| 2011/0258689 A1 | 10/2011 | Cohen et al. |
| 2011/0275940 A1 | 11/2011 | Nims et al. |
| 2012/0015778 A1 | 1/2012 | Lee et al. |
| 2012/0015779 A1 | 1/2012 | Powch et al. |
| 2012/0035487 A1 | 2/2012 | Werner et al. |
| 2012/0046113 A1 | 2/2012 | Ballas |
| 2012/0052802 A1 | 3/2012 | Kasslin et al. |
| 2012/0072165 A1 | 3/2012 | Jallon |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0092157 A1 | 4/2012 | Tran |
| 2012/0094649 A1 | 4/2012 | Porrati et al. |
| 2012/0101952 A1 | 4/2012 | Raleigh et al. |
| 2012/0102008 A1 | 4/2012 | Kaariainen et al. |
| 2012/0108225 A1* | 5/2012 | Luna ............... H04W 28/0215 455/418 |
| 2012/0116684 A1 | 5/2012 | Ingrassia, Jr. et al. |
| 2012/0119911 A1 | 5/2012 | Jeon et al. |
| 2012/0150483 A1 | 6/2012 | Vock et al. |
| 2012/0165684 A1 | 6/2012 | Sholder |
| 2012/0166257 A1 | 6/2012 | Shiragami et al. |
| 2012/0179278 A1 | 7/2012 | Riley et al. |
| 2012/0179754 A1 | 7/2012 | Nilsson et al. |
| 2012/0183939 A1 | 7/2012 | Aragones et al. |
| 2012/0215328 A1 | 8/2012 | Schmelzer |
| 2012/0221634 A1 | 8/2012 | Treu et al. |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0245716 A1 | 9/2012 | Srinivasan et al. |
| 2012/0251079 A1 | 10/2012 | Meschter et al. |
| 2012/0254987 A1 | 10/2012 | Ge et al. |
| 2012/0265477 A1 | 10/2012 | Vock et al. |
| 2012/0265480 A1 | 10/2012 | Oshima |
| 2012/0274508 A1 | 11/2012 | Brown et al. |
| 2012/0283855 A1 | 11/2012 | Hoffman et al. |
| 2012/0289788 A1 | 11/2012 | Jain et al. |
| 2012/0290109 A1 | 11/2012 | Engelberg et al. |
| 2012/0296400 A1 | 11/2012 | Bierman et al. |
| 2012/0297229 A1 | 11/2012 | Desai et al. |
| 2012/0297440 A1 | 11/2012 | Reams et al. |
| 2012/0316406 A1* | 12/2012 | Rahman ............... G01C 22/006 600/595 |
| 2012/0316456 A1 | 12/2012 | Rahman et al. |
| 2012/0324226 A1 | 12/2012 | Bichsel et al. |
| 2012/0330109 A1 | 12/2012 | Tran |
| 2013/0006718 A1 | 1/2013 | Nielsen et al. |
| 2013/0041590 A1 | 2/2013 | Burich et al. |
| 2013/0072169 A1 | 3/2013 | Ross et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0094600 A1 | 4/2013 | Beziat et al. |
| 2013/0095459 A1 | 4/2013 | Tran |
| 2013/0096843 A1 | 4/2013 | Yuen et al. |
| 2013/0102251 A1 | 4/2013 | Linde et al. |
| 2013/0103847 A1 | 4/2013 | Brown et al. |
| 2013/0106684 A1 | 5/2013 | Weast et al. |
| 2013/0109323 A1 | 5/2013 | Ruutu et al. |
| 2013/0110264 A1 | 5/2013 | Weast et al. |
| 2013/0114415 A1* | 5/2013 | Das ............... H04W 16/02 370/336 |
| 2013/0132501 A1 | 5/2013 | Vandwalle et al. |
| 2013/0151193 A1 | 6/2013 | Kulach et al. |
| 2013/0151196 A1 | 6/2013 | Yuen et al. |
| 2013/0158369 A1 | 6/2013 | Yuen et al. |
| 2013/0166048 A1 | 6/2013 | Werner et al. |
| 2013/0173658 A1 | 7/2013 | Adelman et al. |
| 2013/0187789 A1 | 7/2013 | Lowe |
| 2013/0188538 A1 | 7/2013 | Kainulainen et al. |
| 2013/0190008 A1 | 7/2013 | Vathsancam et al. |
| 2013/0190903 A1 | 7/2013 | Balakrishnan et al. |
| 2013/0191034 A1 | 7/2013 | Weast et al. |
| 2013/0203475 A1 | 8/2013 | Kil et al. |
| 2013/0209972 A1 | 8/2013 | Carter et al. |
| 2013/0225117 A1 | 8/2013 | Giacoletto et al. |
| 2013/0228063 A1 | 9/2013 | Turner |
| 2013/0231574 A1 | 9/2013 | Tran |
| 2013/0238287 A1 | 9/2013 | Hoffman et al. |
| 2013/0261475 A1 | 10/2013 | Mochizuki |
| 2013/0267249 A1 | 10/2013 | Rosenberg |
| 2013/0268199 A1 | 10/2013 | Nielsen et al. |
| 2013/0268236 A1 | 10/2013 | Yuen et al. |
| 2013/0268687 A1 | 10/2013 | Schrecker |
| 2013/0268767 A1 | 10/2013 | Schrecker |
| 2013/0274904 A1 | 10/2013 | Coza et al. |
| 2013/0281110 A1 | 10/2013 | Zelinka |
| 2013/0289366 A1 | 10/2013 | Chua et al. |
| 2013/0296666 A1 | 11/2013 | Kumar et al. |
| 2013/0296672 A1 | 11/2013 | O'Neil et al. |
| 2013/0296673 A1 | 11/2013 | Thaveeorungsrioorn et al. |
| 2013/0297220 A1 | 11/2013 | Yuen et al. |
| 2013/0310896 A1 | 11/2013 | Mass |
| 2013/0325396 A1 | 12/2013 | Yuen et al. |
| 2013/0326495 A1 | 12/2013 | Reunamaki et al. |
| 2013/0331058 A1 | 12/2013 | Harvey |
| 2013/0337974 A1 | 12/2013 | Yanev et al. |
| 2013/0345978 A1 | 12/2013 | Lush et al. |
| 2014/0035761 A1 | 2/2014 | Burton et al. |
| 2014/0035764 A1 | 2/2014 | Burton et al. |
| 2014/0039804 A1 | 2/2014 | Park et al. |
| 2014/0039840 A1 | 2/2014 | Yuen et al. |
| 2014/0039841 A1 | 2/2014 | Yuen et al. |
| 2014/0052280 A1 | 2/2014 | Yuen et al. |
| 2014/0067278 A1 | 3/2014 | Yuen et al. |
| 2014/0077673 A1 | 3/2014 | Garg et al. |
| 2014/0085077 A1 | 3/2014 | Luna et al. |
| 2014/0094941 A1 | 4/2014 | Ellis et al. |
| 2014/0099614 A1 | 4/2014 | Hu et al. |
| 2014/0107493 A1 | 4/2014 | Yuen et al. |
| 2014/0121471 A1 | 5/2014 | Walker |
| 2014/0125618 A1 | 5/2014 | Panther et al. |
| 2014/0156228 A1 | 6/2014 | Yuen et al. |
| 2014/0164611 A1 | 6/2014 | Molettiere et al. |
| 2014/0172362 A1 | 6/2014 | Burton et al. |
| 2014/0180022 A1 | 6/2014 | Stivoric et al. |
| 2014/0191866 A1 | 7/2014 | Yuen et al. |
| 2014/0191867 A1 | 7/2014 | Yuen et al. |
| 2014/0200691 A1 | 7/2014 | Lee et al. |
| 2014/0207264 A1 | 7/2014 | Quy |
| 2014/0213858 A1 | 7/2014 | Presura et al. |
| 2014/0273858 A1 | 9/2014 | Panther et al. |
| 2014/0275885 A1 | 9/2014 | Isaacson et al. |
| 2014/0278229 A1 | 9/2014 | Hong et al. |
| 2014/0315491 A1 | 10/2014 | Preiszler et al. |
| 2014/0316305 A1 | 10/2014 | Venkatraman et al. |
| 2014/0337451 A1 | 11/2014 | Choudbary et al. |
| 2014/0337621 A1 | 11/2014 | Nakhimov |
| 2014/0343867 A1 | 11/2014 | Yuen et al. |
| 2015/0026647 A1 | 1/2015 | Park et al. |
| 2015/0057967 A1 | 2/2015 | Albinali |
| 2015/0088457 A1 | 3/2015 | Yuen et al. |
| 2015/0102923 A1 | 4/2015 | Messenger et al. |
| 2015/0120186 A1 | 4/2015 | Heikes |
| 2015/0127268 A1 | 5/2015 | Park et al. |
| 2015/0137994 A1 | 5/2015 | Rahman et al. |
| 2015/0220883 A1 | 8/2015 | B'far et al. |
| 2015/0289081 A1 | 10/2015 | Chen et al. |
| 2015/0289802 A1 | 10/2015 | Thomas et al. |
| 2015/0324541 A1 | 11/2015 | Cheung et al. |
| 2015/0374267 A1 | 12/2015 | Laughlin |
| 2016/0058372 A1 | 3/2016 | Raghuram et al. |
| 2016/0063888 A1 | 3/2016 | Mccallum et al. |
| 2016/0089572 A1 | 3/2016 | Liu et al. |
| 2016/0107646 A1 | 4/2016 | Kolisetty et al. |

(56) References Cited

U.S. PATENT DOCUMENTS

| | | | |
|---|---|---|---|
| 2016/0259426 | A1 | 9/2016 | Yuen et al. |
| 2016/0278669 | A1 | 9/2016 | Messenger et al. |
| 2016/0285985 | A1 | 9/2016 | Molettiere et al. |
| 2016/0323401 | A1 | 9/2016 | Messenger et al. |
| 2017/0257162 | A1 | 9/2017 | Panther et al. |

FOREIGN PATENT DOCUMENTS

| | | |
|---|---|---|
| CN | 102067560 | 5/2011 |
| CN | 102111434 | 6/2011 |
| CN | 102377815 | 3/2012 |
| CN | 102740933 | 10/2012 |
| CN | 102983890 | 3/2013 |
| CN | 103226647 | 7/2013 |
| EP | 1721237 | 11/2006 |
| JP | 11347021 | 12/1999 |
| RU | 2178588 | 1/2002 |
| WO | WO 2002/011019 | 2/2002 |
| WO | WO 2006/055125 | 5/2006 |
| WO | WO 2006/090197 | 8/2006 |
| WO | WO 2008/038141 | 4/2008 |
| WO | WO 2009/042965 | 4/2009 |
| WO | WO 2012/061438 | 5/2012 |
| WO | WO 2012/170924 | 12/2012 |
| WO | WO 2012/171032 | 12/2012 |
| WO | WO 2012/170586 | 2/2013 |
| WO | WO 2015/127067 | 8/2015 |
| WO | WO 2016/003269 | 1/2016 |

OTHER PUBLICATIONS

"Parts of Your Band," (Product Release Date Unknown, downloaded Jul. 22, 2013) Jawbone UP Band, page.
Chandrasekar et al., "Plug-and-Play, Single-Chip Photoplethysmography", 34th Annual International Conference of the IEEE EMBS, San Dieqo, California USA, Aug. 28-Sep. 1, 2012, 4 pages.
Chinese First Office Action, dated Jul. 27, 2017, issued in Application No. CN 201410242747.8.
Chinese Second Office Action, dated Mar. 27, 2018, issued in Application No. CN 201410242747.8.
Chinese Third Office Action, dated Jul. 4, 2018, issued in Application No. CN 201410242747.8.
Chudnow, Alan (Dec. 3, 2012) "Basis Wristband Make Its Debut," The Wired Self, Living in a Wired World, published in Health [retrieved on Jul. 22, 2013 at http://thewiredself.com/health/basis-wrist-band-make-its-debut/], 3pp.
Clifford et al., "Altimeter and Barometer System", Freescale Semiconductor Application Note AN1979, Rev. 3, Nov. 2006, 10 pages.
Definition of "Graphic" from Merriam-Webster Dictionary, downloaded from merriam-webster.com on Oct. 4, 2014, 3 pp.
Definition of "Graphical user interface" from Merriam-Webster Dictionary, downloaded from merriam-webster.com on Oct. 4, 2014, 2 pp.
DesMarais, Christina (posted on Sep. 3, 2013) "Which New Activity Tracker is Best for You?" Health and Home, Health & Fitness , Guides & Reviews, [Retrieved on Sep. 23, 2013 at http://www.techlicious.com/guide/which-new-activity-tracker-is-right-for--you/] 4 pp.
Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.
Fang et al, "Design of a Wireless Assisted Pedestrian Dead Reckoning System—The NavMote Experience", IEEE Transactions on Instrumentation and Measurement, vol. 54, No. 6, Dec. 2005, pp. 2342-2358.
Fitbit Inc., "Fitbit Automatically Tracks Your Fitness And Sleep" published online at web.archive.org/web/20080910224820/http://www.fitbit.com, downloaded Sep. 10, 2008, 1 page.

Fitbit User's Manual, Last Updated Oct. 22, 2009, 15 pages.
Forerunner® 10 Owner's Manual (Aug. 2012), Garmin Ltd., 10 pp.
Forerunner® 110 Owner's Manual, (2010) "GPS-Enabled Sport Watch," Garmin Ltd., 16 pp.
Forerunner® 201 personal trainer owner's manual, (Feb. 2006) Garmin Ltd., 48 pp.
Forerunner® 205/305 Owner's Manual, GPS-enabled trainer for runners, (2006-2008), Garmin Ltd., 80 pp.
Forerunner® 210 Owner's Manual, (2010) "GPS-Enabled Sport Watch," Garmin Ltd., 28 pp.
Forerunner® 301 personal trainer owner's manual, (Feb. 2006) Garmin Ltd., 66 pp.
Forerunner® 310XT Owner's Manual, Multisport GPS Training Device, (2009-2013), Garmin Ltd., 56 pp.
Forerunner® 405 Owner's Manual, (Mar. 2011) "GPS-Enabled Sport Watch With Wireless Sync," Garmin Ltd., 56 pp.
Forerunner® 405CX Owner's Manual, "GPS-Enabled Sports Watch With Wireless Sync," (Mar. 2009), Garmin Ltd., 56 pp.
Forerunner® 410 Owner's Manual, (Jul. 2012) "GPS-Enabled Sport Watch With Wireless Sync," Garmin Ltd., 52 pp.
Forerunner® 50 with ANT+Sport. TM. wireless technology, Owner's Manual, (Nov. 2007) Garmin Ltd., 44 pp.
Forerunner® 910XT Owner's Manual, (Jan. 2013) Garmin Ltd., 56 pp.
Garmin Swim™ Owner's Manual (Jun. 2012), 12 pp.
Godfrey et al., "Direct Measurement of Human Movement by Accelerometry", Medical Engineering & Physics, vol. 30, 2008, pp. 1364-1386 (22 pages).
Godha et al., "Foot Mounted Inertia System for Pedestrian Navigation", Measurement Science and Technology, vol. 19, No. 7, May 2008, pp. 1-9 (10 pages).
Intersema, "Using MS5534 for altimeters and barometers", Application Note AN501, Jan. 2006, 12pages.
Ladetto et al, "On Foot Navigation: When GPS alone is not Enough", Journal of Navigation, vol. 53, No. 2, Sep. 2000, pp. 279-285 (6 pages).
Lammel et al., "Indoor Navigation with MEMS Sensors", Proceedings of the Eurosensors XIII conference, vol. 1, No. 1, Sep. 2009, pp. 532-535 (4 pages).
Lark/Larkpro, User Manual, (2012) "What's in the box," Lark Technologies, 7 pp.
Larklife, User Manual, (2012) Lark Technologies, 7 pp.
Lester et al, "Validated caloric expenditure estimation using a single body—worn sensor", Proc. of the Int'l Conf. on Ubiquitous Computing, 2009, pp. 225-234 (10 pages).
Lester et al., "A Hybrid Discriminative/Generative Approach for Modeling Human Activities", Proc. of the Int'l Joint Conf. Artificial Intelligence, 2005, pp. 766-772 (7 pages).
Minetti et al. Energy cost of walking and running at extreme uphill and downhill slopes. J Appl Physiol. 2002: 93:10-39-1046.
Nike+ Fuel Band GPS Manual, User's Guide (Product Release Date Unknown, downloaded Jul. 22, 2013), 26 pages.
Nike+SportBand User's Guide, (Product Release Date Unknown, downloaded Jul. 22, 2013), 36 pages.
Nike+SportWatch GPS Manual, User's Guide, Powered by TOMTOM, (Product Release Date Unknown, downloaded Jul. 22, 2013), 42 pages.
O'Donovan et al., 2009, A context aware wireless body area network (BAN), Proc. 3rd Intl. Conf. Pervasive Computing Technologies for Healthcare, pp. 1-8.
Ohtaki et al, "Automatic classification of ambulatory movements and evaluation of energy consumptions utilizing accelerometers and barometer", Microsystem Technologies, vol. 11, No. 8-10, Aug. 2005, pp. 1034-1040 (7 pages).
Parkka, et al, Activity Classification Using Realistic Data From Wearable Sensors, IEEE Transactions on Information Technology in Biomedicine, vol. 10, No. 1, Jan. 2006, pp. 119-128 (10pages).
PCT/IB07/03617 International Search Report issued on Aug. 15, 2008, in related application, 3 pages.
Perrin et al, "Improvement of Walking Speed Prediction by Accelerometry and Altimetry, Validated by Satellite Positioning", Medical & Biological Engineering & Computing, vol. 38, 2000, pp. 164-168 (5 pages).

(56) References Cited

OTHER PUBLICATIONS

Polar WearLink® + Coded Transmitter 31 Coded Transmitter W.I.N.D. User Manual, POLAR® Listen to Your Body, Manufactured by Polar Electro Oy, 11 pages.
Rainmaker, (Jun. 25, 2012, updated Feb. 16, 2013) "Garmin Swim watch In-Depth Review," [retrieved on Sep. 9, 2013 at http://www.dcrainmaker.com/2012/06/garmin-swim-in-depth-review.html, 38 pp.
Retscher, "An Intelligent Multi-Sensor system for Pedestrian Navigation", Journal of Global Positioning Systems, vol. 5, No. 1, 2006, pp. 110-118 (9 pages).
Sagawa et al, "Classification of Human Moving Patterns Using Air Pressure and Acceleration", Proceedings of the 24th Annual Conference of the IEEE Industrial Electronics Society, vol. 2, Aug.-Sep. 1998, pp. 1214-1219, 6 pages.
Sagawa et al, "Non-restricted measurement of walking distance", IEEE Int'l Conf. on Systems, Man, and Cybernetics, vol. 3, Oct. 2000, pp. 1847-1852 6 pages.
Specification of the Bluetooth® System, Core Package, version 4.1, Dec. 2013, vols. O & 1, 282 pages.
Stirling et al., "Evaluation of a New Method of Heading Estimation of Pedestrian Dead Reckoning Using Shoe Mounted Sensors", Journal of Navigation, vol. 58, 2005, pp. 31-45 15 pages.
Suunto LUMI, "User Guide", Copyright June and Sep. 2007, 49 pages.
Tanigawa et al, "Drift-Free Dynamic Height Sensor Using MEMS IMU Aided By MEMS Pressure Sensor", Workshop on Positioning, Navigation and Communication, Mar. 2008, pp. 191-196 6 pages.
Thompson et al., (Jan. 1996) "Predicted and measured resting metabolic rate of male and female endurance athletes," Journal of the American Dietetic Association 96(1):30-34.
US Final Office Action, dated Jun. 10, 2016, issued in U.S. Appl. No. 14/290,902.
US Final Office Action, dated May 4, 2015, issued in U.S. Appl. No. 14/290,902.
US Final Office Action, dated Sep. 10, 2014, issued in U.S. Appl. No. 13/167,742.
US Notice of Allowance, dated Dec. 21, 2016, issued in U.S. Appl. No. 14/290,902.
US Notice of Allowance, dated Feb. 20, 2013, issued in U.S. Appl. No. 13/667,242.
US Notice of Allowance, dated Jan. 17, 2013, issued in U.S. Appl. No. 13/667,229.
US Notice of Allowance, dated Jul. 12, 2012, issued in U.S. Appl. No. 13/469,033.
US Notice of Allowance, dated Jul. 19, 2012, issued in U.S. Appl. No. 13/469,027.
US Notice of Allowance, dated Jun. 16, 2014, issued in U.S. Appl. No. 14/076,527.
US Notice of Allowance, dated Jun. 5, 2013, issued in U.S. Appl. No. 13/693,334.
US Notice of Allowance, dated Jun. 5, 2013, issued in U.S. Appl. No. 13/759,485.
US Notice of Allowance, dated May 24, 2013, issued in U.S. Appl. No. 13/767,836.
US Notice of Allowance, dated Nov. 5, 2018, issued in U.S. Appl. No. 15/465,411.
US Notice of Allowance, dated Oct. 10, 2014, issued in U.S. Appl. No. 14/448,879.
US Notice of Allowance, dated Oct. 15, 2012, issued in U.S. Appl. No. 13/297,165.
US Notice of Allowance, dated Oct. 25, 2013, issued in U.S. Appl. No. 13/913,726.
US Notice of Allowance, dated Sep. 25, 2013, issued in U.S. Appl. No. 13/913,744.
US Office Action, dated Apr. 10, 2012, issued in U.S. Appl. No. 13/297,165.
US Office Action, dated Apr. 19, 2013, issued in U.S. Appl. No. 13/759,485.
US Office Action, dated Feb. 12, 2018, issued in U.S. Appl. No. 15/465,411.
US Office Action, dated Feb. 2, 2012, issued in U.S. Appl. No. 13,246,843.
US Office Action, dated Jan. 16, 2013, issued in U.S. Appl. No. 13/667,242.
US Office Action, dated Jan. 17, 2013, issued in U.S. Appl. No. 13/674,265.
US Office Action, dated Jul. 23, 2018, issued in U.S. Appl. No. 15/465,411.
US Office Action, dated Mar. 14, 2014, issued in U.S. Appl. No. 14/076,527.
US Office Action, dated Mar. 18, 2013, issued in U.S. Appl. No. 13/167,742.
US Office Action, dated May 7, 2014, issued in U.S. Appl. No. 13/167,742.
US Office Action, dated Nov. 19, 2014, issued in U.S. Appl. No. 14/290,902.
US Office Action, dated Nov. 29, 2013, issued in U.S. Appl. No. 13/167,742.
US Office Action, dated Oct. 21, 2015, issued in U.S. Appl. No. 14/290,902.
US Office Action, dated Sep. 11, 2013, issued in U.S. Appl. No. 13/913,744.
US Office Action, dated Sep. 20, 2013, issued in U.S. Appl. No. 13/913,726.
VTI Technologies, "SCP 1000-001/011 Pressure Sensor as Barometer and Altimeter", Application Note 33, Jun. 2006, 3 pages.

* cited by examiner

METHODS, SYSTEMS AND DEVICES FOR GENERATING REAL-TIME ACTIVITY DATA UPDATES TO DISPLAY DEVICES

CLAIM OF PRIORITY

This application is a continuation of pending U.S. patent application Ser. No. 14/050,301, filed on Oct. 9, 2013, and entitled "Methods, Systems and Devices for Generating Real-Time Activity data updates to Display Devices," which claims priority from expired U.S. Provisional Application No. 61/885,966, entitled "Methods, Systems and Devices for Generating Real-Time Activity Data Updates to Display Devices," filed on Oct. 2, 2013, which is herein incorporated by reference.

U.S. patent application Ser. No. 14/050,301, filed on Oct. 9, 2013 is a continuation-in-part of pending U.S. patent application Ser. No. 13/959,714, (now U.S. Pat. No. 8,762,101, issued on Jun. 24, 2014), filed on Aug. 5, 2013, titled "Methods and Systems for Identification of Event Data Having Combined Activity and Location Information of Portable Monitoring Devices."

U.S. patent application Ser. No. 13/959,714, filed on Aug. 5, 2013 is a continuation-in-part of U.S. patent application Ser. No. 13/693,334 (now U.S. Pat. No. 8,548,770, issued on Oct. 1, 2013), filed on Dec. 4, 2012, titled "Portable Monitoring Devices and Methods for Operating Same."

U.S. patent application Ser. No. 13/693,334 is a divisional of U.S. patent application Ser. No. 13/667,229 (now issued as U.S. Pat. No. 8,437,980, issued on May 7, 2013), filed on Nov. 2, 2012, titled "Portable Monitoring Devices and Methods for Operating Same."

U.S. patent application Ser. No. 13/667,229 is a divisional of U.S. patent application Ser. No. 13/469,027 (now U.S. Pat. No. 8,311,769, issued on Nov. 13, 2012), filed on May 10, 2012, titled "Portable Monitoring Devices and Methods for Operating Same."

U.S. patent application Ser. No. 13/469,027 is a divisional of U.S. patent application Ser. No. 13/246,843, (now U.S. Pat. No. 8,180,591, issued on May 15, 2012), filed on Sep. 27, 2011.

U.S. patent application Ser. No. 13/246,843 is a divisional of pending U.S. patent application Ser. No. 13/156,304, (now U.S. Pat. No. 9,167,991, issued on Oct. 27, 2015) filed on Jun. 8, 2011, titled "Portable Monitoring Devices and Methods for Operating Same", which claims the benefit of and priority to, under 35 U.S.C. 119§ (e), to expired U.S. Provisional Patent Application No. 61/388,595, filed on Sep. 30, 2010, and titled "Portable Monitoring Devices and Methods for Operating Same", and to expired U.S. Provisional Patent Application No. 61/390,811, filed on Oct. 7, 2010, and titled "Portable Monitoring Devices and Methods for Operating Same," all of which are hereby incorporated by reference in their entirety.

This application is a continuation of pending U.S. patent application Ser. No. 14/050,301, filed on Oct. 9, 2013, and entitled "Methods, Systems and Devices for Generating Real-Time Activity data updates to Display Devices," which is a continuation-in-part of pending U.S. patent application Ser. No. 13/959,714, (now U.S. Pat. No. 8,762,101, issued on Jun. 24, 2014), filed Aug. 5, 2013, titled "Methods and Systems for Identification of Event Data Having Combined Activity and Location Information of Portable Monitoring Devices."

U.S. patent application Ser. No. 13/959,714 is a continuation-in-part of U.S. patent application Ser. No. 13/759,485, (now issued as U.S. Pat. No. 8,543,351, issued on Sep. 24, 2013), filed on Feb. 5, 2013, titled "Portable Monitoring Devices and Methods for Operating Same."

U.S. patent application Ser. No. 13/759,485 is a divisional of U.S. patent application Ser. No. 13/667,229, (now issued as U.S. Pat. No. 8,437,980, issued on May 7, 2013), filed on Nov. 2, 2012, titled "Portable Monitoring Devices and Methods for Operating Same."

U.S. patent application Ser. No. 13/667,229 is a divisional of U.S. patent application Ser. No. 13/469,027, now U.S. Pat. No. 8,311,769, issued on Nov. 13, 2012, filed on May 10, 2012, titled "Portable Monitoring Devices and Methods for Operating Same."

U.S. patent application Ser. No. 13/469,027 is a divisional of U.S. patent application Ser. No. 13/246,843, now U.S. Pat. No. 8,180,591, issued on May 15, 2012, filed on Sep. 27, 2011.

U.S. patent application Ser. No. 13/246,843 is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§ (e), to expired U.S. Provisional Patent Application No. 61/388,595, filed on Sep. 30, 2010, and titled "Portable Monitoring Devices and Methods for Operating Same" and to expired U.S. Provisional Patent Application No. 61/390,811, filed on Oct. 7, 2010, and titled "Portable Monitoring Devices and Methods for Operating Same."

All above listed applications and patents are hereby incorporated by reference in their entirety.

CROSS REFERENCE TO RELATED APPLICATION

This Application is related to pending U.S. application Ser. No. 14/050,292, filed on Oct. 9, 2013, now U.S. Pat. No. 8,744,803, entitled "Methods, Systems, and Devices for Activity Tracking Device Data Synchronization with Computing Devices," which claims priority to expired U.S. Provisional Application No. 61/885,962, filed on Oct. 2, 2013, both of which are incorporated herein by reference.

FIELD

The present disclosure relates to systems and methods for capturing activity data over a period of time and synchronizing data transfers between a tracker device and a client device.

BACKGROUND

In recent years, the need for health and fitness has grown tremendously. The growth has occurred due to a better understanding of the benefits of good fitness to overall health and wellness. Unfortunately, although today's modern culture has brought about many new technologies, such as the Internet, connected devices and computers, people have become less active. Additionally, many office jobs require people to sit in front of computer screens for long periods of time, which further reduces a person's activity levels. Furthermore, much of today's entertainment options involve viewing multimedia content, computer social networking, and other types of computer involved interfacing. Although such computer activity can be very productive as well as entertaining, such activity tends to reduce a person's overall physical activity.

To provide users concerned with health and fitness a way of measuring or accounting for their activity or lack thereof, fitness trackers are often used. Fitness trackers are used to measure activity, such as walking, motion, running, sleeping, being inactive, bicycling, exercising on an elliptical trainer, and the like. Usually, the data collected by such fitness trackers can be transferred and viewed on a computing device. However, such data is often provided as a basic accumulation of activity data with complicated or confusing interfaces. In addition, updates between a tracker and a client device usually require wired connectors and/or complex syncing schemes.

It is in this context that embodiments described herein arise.

SUMMARY

Embodiments described in the present disclosure provide systems, apparatus, computer readable media, and methods for tracking activity data of a user and enabling the display of the activity to a computing device in substantial real-time. The activity data displayed can be a metric, which is shown to numerically increase on the computing device as the user engages in activity that is tracked. In some embodiments, the data need not numerically increase, but can simply change or update. In one example, as the user engages in walking, a step count metric can be shown to change and/or increase as the user is walking. In one embodiment, the transfer rates for sending real-time updates can be set by scaling the connection interval of data transfers up or down, depending on the type/amount of data to be transferred in accordance with an update condition.

In one embodiment, a method is provided. The method includes capturing motion data associated with activity of a user via an activity tracking device. The motion data is quantified into a plurality of metrics associated with the activity of the user. The method storing the motion data in storage of the activity tracking device. The method connects the activity tracking device with a computing device over a wireless data connection, and sending motion data to the computing device for display of a metric, of the plurality of metrics, on a graphical user interface of an activity application of the computing device. The sending of motion data to the computing device is configured to continue while additional motion data is captured and sent to the computing device. The metric displayed on the graphical user interface is shown to change in an increasing numerical or graphical form in substantial real-time. The method being executed by a processor.

In another embodiment, a device configured for capture of activity for a user and cause the display of activity data in substantial real-time is provided. The device includes a housing and a sensor disposed in the housing to capture motion data associated with activity of the user via a device. The motion data is captured over time, and the motion data is quantified to define a plurality of metrics associated with the activity of the user. The device includes a memory for storing the captured motion data. The device also includes a processor for managing connection of the device with a computing device over a wireless data connection. The processor manages sending of motion data to the computing device for display of a metric, of the plurality of metrics, on a graphical user interface of an activity application of the computing device. The sending of motion data to the computing device is configured to continue while additional motion data is captured and sent to the computing device. The metric is configured to be displayed on the graphical user interface is shown to change in an increasing numerical or graphical form in substantial real-time.

In still another embodiment, a wrist attachable device is disclosed. The device includes a battery, an altimeter for producing altitude data, an accelerometer for capturing motion data associated with activity of a user, and a screen for displaying data. The data including metrics that quantify the captured motion data and altitude data. The screen having dead front operation that is configured to remain in an off-state until activated. The device further including a communication circuit for enabling wireless communication with a computing device and a memory for storing the captured motion data and altitude data. Further included is a processor for managing connection of the wrist attachable device with the computing device. The processor further managing sending data to the computing device for display of a metric on a graphical user interface of an activity application of the computing device. The sending of data to the computing device is configured to continue while additional data that is displayable is available for sending. The metric displayed on the graphical user interface is shown to change in state in substantial real-time, in response to data sent from the wrist attachable device to the device.

Computer readable medium for storing program instructions executable by a processor, for managing the transfer of data between an activity tracking device and a computing device client is also provided.

Other aspects will become apparent from the following detailed description, taken in conjunction with the accompanying drawings, illustrating by way of example the principles of embodiments described in the present disclosure.

BRIEF DESCRIPTION OF THE DRAWINGS

Various embodiments described in the present disclosure may best be understood by reference to the following description taken in conjunction with the accompanying drawings.

DETAILED DESCRIPTION

Figure 1A:
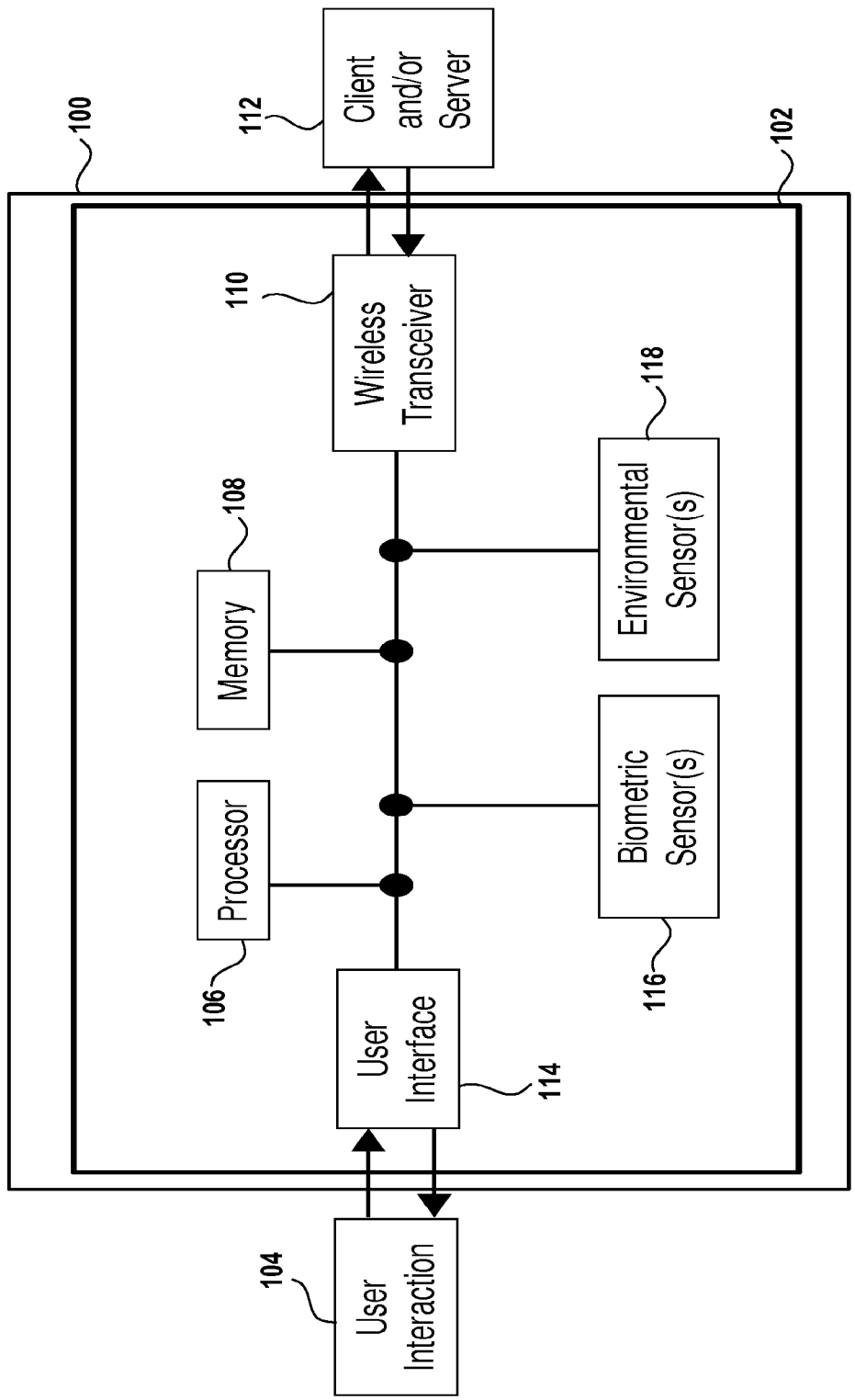
FIG. 1A shows a block diagram of an activity tracking device, in accordance with one embodiment of the present invention.

Embodiments described in the present disclosure provide systems, apparatus, computer readable media, and methods for tracking activity data of a user and enabling the display of the activity to a computing device in substantial real-time. The activity data displayed can be a metric, which is shown to change and/or numerically increase on the computing device as the user engages in activity that is tracked. For instance, as the user engages in walking, a step count metric can be shown to change and increase as the user is walking. In one embodiment, the connection interval for data transfers to and from an activity tracking device can be scaled, depending on an update condition.

The computing device can be a computer that executes an activity tracking application (APP). The computing device can take on any form, so long as it can process information, load and execute an application, and can communicate wirelessly with the activity tracking device. For example purposes, the computing device can be a computer, a tablet computer, a smart phone, a tablet, a laptop, a desktop, a watch computer, glasses computer, or any device having access to memory and processing power.

The scaling of the connection interval enables dynamic setting of a data transfer rate between the activity tracking device and the computing device, based on a determined update condition. The update condition can include detecting that an application (e.g., activity tracking application) on the computing device has been opened, which causes a first transfer rate to be set. The first transfer rate has a scaled-up connection interval which allows for a higher frequency of packets to be sent between the activity tracking device and the computing device (e.g., changes the packet transfer frequency).

The scaled-up connection interval of the first transfer rate enables larger blocks of data and/or data logs to be downloaded faster from the activity tracking device to the computing device, so as to enable display of tracked or monitored information collected when the application was not open or the computing device was not in wireless connection range with the activity tracking device. In some embodiments, the scaled-up connection interval also enables transfer of data for firmware updates of the device, when updates are needed, scheduled or required. In one configuration, if the update conditions dictate that the activity tracking device is generating data that can be transferred to the computing device, while the application is open, the connection interval can be scaled-down to set a second data transfer rate between the activity tracking device and the computing device. In one embodiment, during the first transfer rate, the transfer of data from the activity tracking device is set directly to the site, e.g., storage associated with a website that manages accounts concerning activity tracking information. In some embodiments, the computing device acts as a transfer pipe between the activity tracking device and the website.

The second transfer rate is used to transfer updates to enable definition of metrics regarding the monitored or captured activity data. In the scaled-down connection interval, the data transfer rate is slower than the scaled-up connection interval, but the amount of data to be transferred is typically less or is data that is just detected/monitored by the activity tracking device. Thus, the second transfer rate of the scaled-down connection interval is sufficient to enable transfer of updates for activity data captured, monitored, or collected by the activity tracking device to the computing device. The transfers of updates enable such activity data to be processed by the computing device and displayed in substantial real-time on a screen of the computing device, just as the activity is occurring and the connection between the activity tracking device and computing device can be maintained. In one embodiment, the second transfer rate is sufficient to enable an external device (e.g., computing device, smartphone, tablet, laptop, desktop, watch computer, glasses computer, etc.) to serve as a real time data display.

Furthermore, the transferred data need not be only motion data or activity data, but the data can include any type of data, such as altitude or relative altitude data, barometric pressure data, heart rate data, temperature data, alarm data, goal data, history status data, processed data, raw data, etc.

Additionally, although the computing device may usually have access to an Internet connection, every transfer between the activity tracking device and the computing device does not require Internet connection. When the computing device is connected to the Internet, the computing device can then sync data to a server. The server, in one embodiment, can be one or more distributed servers, data centers, virtualized servers in distributed data centers, etc. The server, in one embodiment, executes an activity management application that enables user account access to metrics associated with activity tracking devices.

It should be noted that there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Further, in the course of describing and illustrating the present inventions, various circuitry, architectures, structures, components, functions and/or elements, as well as combinations and/or permutations thereof, are set forth. It should be understood that circuitry, architectures, structures, components, functions and/or elements other than those specifically described and illustrated, are contemplated and are within the scope of the present inventions, as well as combinations and/or permutations thereof FIG. 1A shows a block diagram of an activity tracking device 100, in accordance with one embodiment of the present invention. The activity tracking device 100 is contained in a housing, which may be worn or held by a user. The housing may be in the form of a wristband, a clip on device, a wearable device, or may be held by the user either in the user's hand or in a pocket or attached to the user's body. The activity tracking device 100 includes device components 102, which may be in the form of logic, storage, and glue logic, one or more processors, microelectronics, and interfacing circuitry. In one example, the components 102 will include a processor 106, memory 108, a wireless transceiver 110, a user interface 114, biometric sensors 116, and environmental sensors 118.

The environmental sensors 118 may be in the form of motion detecting sensors. In some embodiments, a motion sensor can be one or more of an accelerometer, or a gyroscope, or a rotary encoder, or a calorie measurement sensor, or a heat measurement sensor, or a moisture measurement sensor, or a displacement sensor, or an ultrasonic sensor, or a pedometer, or an altimeter, or a linear motion sensor, or an angular motion sensor, or a multi-axis motion sensor, or a combination thereof. The biometric sensors 116 can be defined to measure physiological characteristics of the user that is using the activity tracking device 100. The user interface 114 provides a way for communicating with the activity tracking device 100, in response to user interaction 104. The user interaction 104 can be in the form of physical contact (e.g., without limitation, tapping, sliding, rubbing, multiple taps, gestures, etc.).

In some embodiments, the user interface 114 is configured to receive user interaction 104 that is in the form of noncontact input. The noncontact input can be by way of proximity sensors, button presses, touch sensitive screen inputs, graphical user interface inputs, voice inputs, sound inputs, etc. The activity tracking device 100 can communicate with a client and/or server 112 using the wireless transceiver 110. The wireless transceiver 110 will allow the activity tracking device 100 to communicate using a wireless connection, which is enabled by wireless communication logic. The wireless communication logic can be in the form of a circuit having radio communication capabilities. The radio communication capabilities can be in the form of a Wi-Fi™ connection, a BLUETOOTH™ connection, a low-energy BLUETOOTH™ connection, or any other form of wireless tethering or near field communication. In still other embodiments, the activity tracking device 100 can communicate with other computing devices using a wired connection (not shown). As mentioned, the environmental sensors 118 can detect motion of the activity tracking device 100.

The motion can be activity of the user, such as walking, running, stair climbing, etc. The motion can also be in the form of physical contact received on any surface of the activity tracking device 110, so long as the environmental sensors 118 can detect such motion from the physical contact. As will be explained in more detail below, the physical contact may be in the form of a tap or multiple taps by a finger upon the housing of the activity tracking device 100.

Figure 1B:
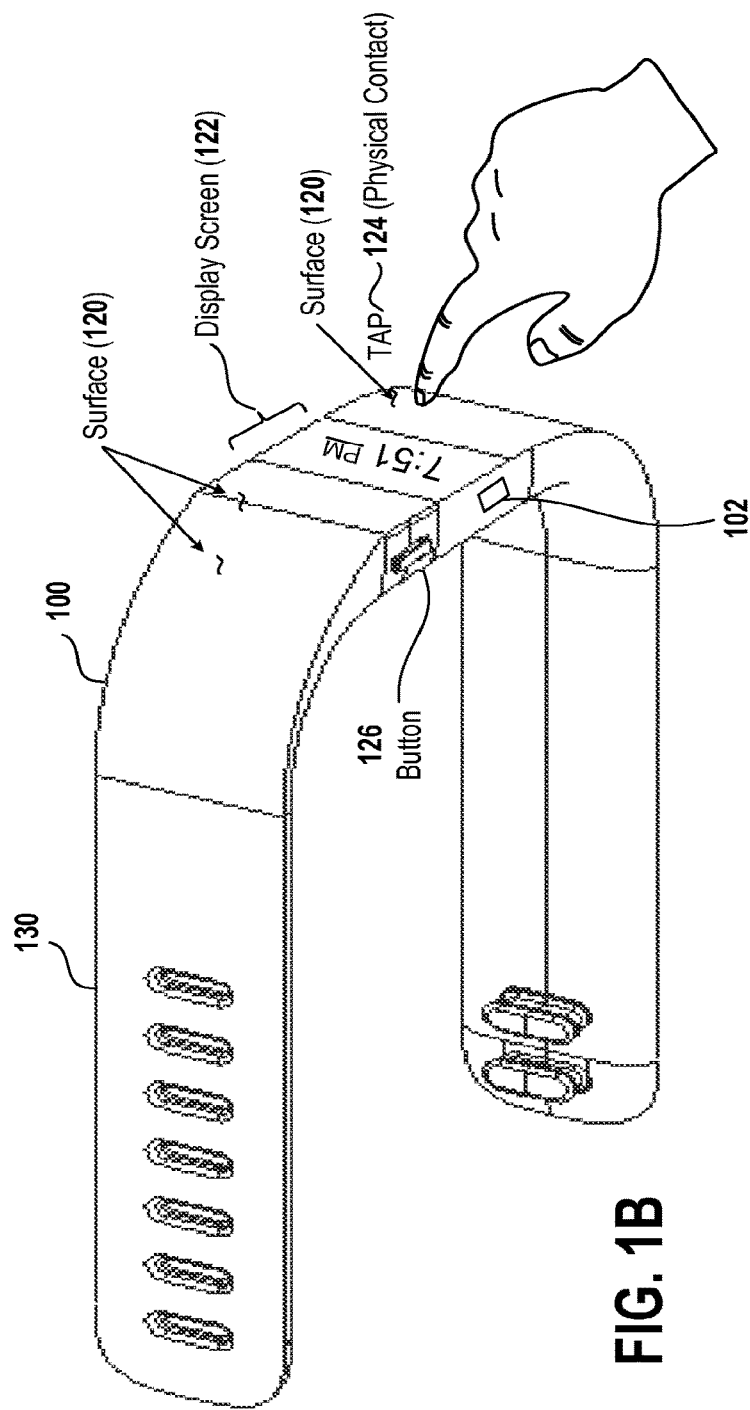
FIG. 1B illustrates an example of an activity tracking device, in accordance with one embodiment of the present invention.

FIG. 1B illustrates an example of an activity tracking device 100 having a housing 130 in the form of a wearable wrist attachable device. The sensors of the activity tracking device 100 can, as mentioned above, detect motion such as physical contact that is applied and received on a surface 120 of the housing 130. In the example shown, the physical contact 124 is in the form of a tap or multiple taps on the surface 120. Device components 102 are, in one embodiment, contained within the housing 130. The location at which the device components 102 are integrated into the housing 130 can vary. For example, the device components 102 can be integrated throughout various locations around the housing 130, and not limited to the central portion of the wrist attachable device. In some embodiments, the device components 102 can be integrated into or with a smart watch device.

In other embodiments, the device components 102 are positioned substantially in a central position of the wrist attachable device, such as under or proximate to a location where a display screen 122 is located. In the illustrated example, the housing 130 also includes a button 126. The button 126 can be pressed to activate the display screen 122, navigate to various metrics displayed on the screen 122, or turn off the screen 122.

Figure 1C:
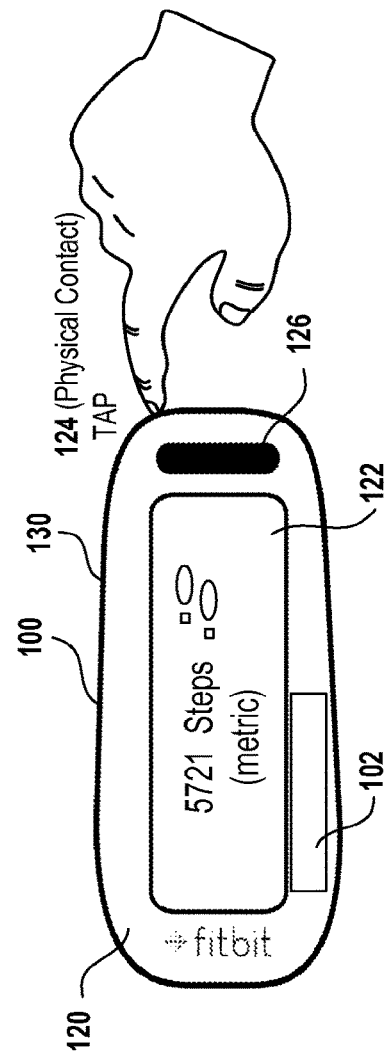
FIG. 1C illustrates another example of an activity tracking device, in accordance with one embodiment of the present invention.

FIG. 1C illustrates another example of an activity tracking device 100, in accordance with one embodiment of the present invention. The form factor of the activity tracking device 100 is shown as a clickable device that includes a screen 122, a button 126, and device components 102 integrated within the housing 130. The housing 130 can include a clip that allows for attachment to clothing or articles of the user, or to simply place the device within a pocket or holder of the user. Accordingly, the physical contact 124 shown with respect to FIG. 1B can also be implemented upon the surface 120 of activity tracking device 100 of FIG. 1C. It should be understood, therefore, that the form factor of the activity tracking device 100 can take on various configurations and should not be limited to the example configurations provided herein.

Figure 2:
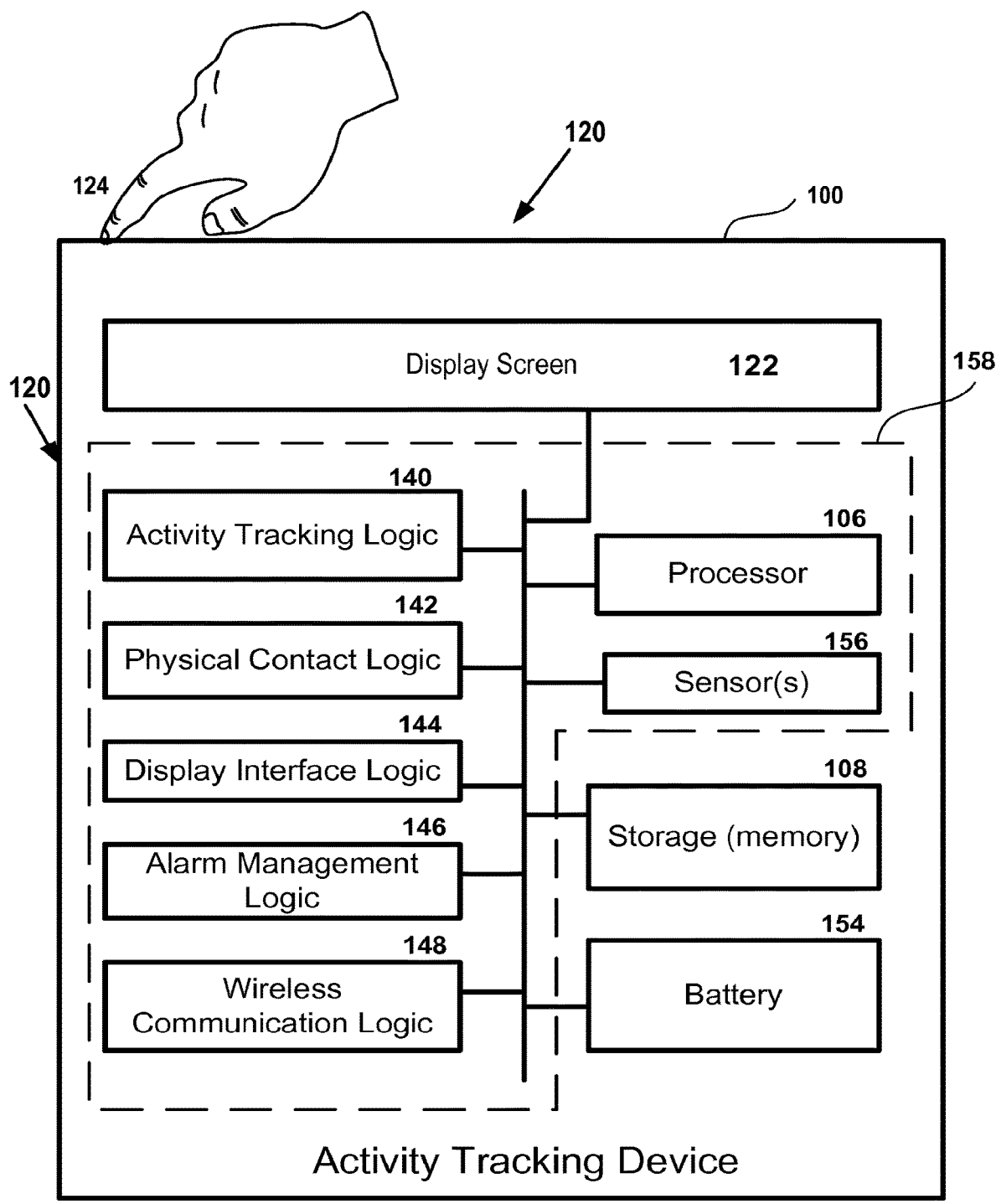
FIG. 2 illustrates an example of activity tracking device including example components utilized for tracking activity and motion of the device, and associated interfaces to a display screen, in accordance with one embodiment of the present invention.

FIG. 2 illustrates an example of activity tracking device 100 of FIG. 1A, showing some additional example components utilized for tracking activity and motion of the device, and associated interfaces to display screen 122. In this example, the finger of a user can be used to tap and provide physical contact 124 onto any surface 120 of activity tracking device 100. The physical contact, when sensed by sensors 156 of the activity tracking device 100, will cause a response by the activity tracking device 100, and therefore provide some metric on the display screen 122. In one embodiment, examples of a display screen 122 can include, but are not limited to, liquid crystal display (LCD) screens, light emitting diode (LED) screens, organic light emitting diode (OLED) screens, plasma display screens, etc.

As shown in FIG. 2, the activity tracking device 100 includes logic 158. Logic 158 may include activity tracking logic 140, physical contact logic 142, display interface logic 144, alarm management logic 146, wireless communication logic 148, processor 106, and sensors 156. Additionally, storage (e.g. memory) 108, and a battery 154 can be integrated within the activity tracking device 100. The activity tracking logic 140 can include logic that is configured to process motion data produced by sensors 156, so as to quantify the motion and produce identifiable metrics associated with the motion.

Some motions will produce and quantify various types of metrics, such as step count, stairs climbed, distance traveled, very active minutes, calories burned, etc. The physical contact logic 142 can include logic that calculates or determines when particular physical contact can qualify as an input. To qualify as an input, the physical contact detected by sensors 156 should have a particular pattern that is identifiable as input. For example, the input may be predefined to be a double tap input, and the physical contact logic 142 can analyze the motion to determine if a double tap indeed occurred in response to analyzing the sensor data produced by sensors 156.

In other embodiments, the physical contact logic can be programmed to determine when particular physical contacts occurred, the time in between the physical contacts, and whether the one or more physical contacts will qualify within predefined motion profiles that would indicate that an input is desired. If physical contact occurs that is not within some predefined profile or pattern, the physical contact logic will not indicate or qualify that physical contact as an input.

The display interface logic 144 is configured to interface with the processor and the physical contact logic to determine when specific metric data will be displayed on the display screen 122 of the activity tracking device 100. The display interface logic 144 can act to turn on the screen, display metric information, display characters or alphanumeric information, display graphical user interface graphics, or combinations thereof. Alarm management logic 146 can function to provide a user interface and settings for managing and receiving input from a user to set an alarm. The alarm management logic can interface with a timekeeping module (e.g., clock, calendar, time zone, etc.), and can trigger the activation of an alarm. The alarm can be in the form of an audible alarm or a non-audible alarm.

A non-audible alarm can provide such alarm by way of a vibration. The vibration can be produced by a motor integrated in the activity tracking device 100. The vibration can be defined to include various vibration patterns, intensities, and custom set patterns. The vibration produced by the motor or motors of the activity tracking device 100 can be managed by the alarm management logic 146 in conjunction with processing by the processor 106. The wireless communication logic 148 is configured for communication of the activity tracking device with another computing device by way of a wireless signal. The wireless signal can be in the form of a radio signal. As noted above, the radio signal can be in the form of a Wi-Fi™ signal, a BLUETOOTH™ signal, a low energy BLUETOOTH™ signal, or combinations thereof The wireless communication logic can interface with the processor 106, storage 108 and battery 154 of device 100, for transferring activity data, which may be in the form of motion data or processed motion data, stored in the storage 108 to the computing device.

In one embodiment, processor 106 functions in conjunction with the various logic components 140, 142, 144, 146, and 148. The processor 106 can, in one embodiment, provide the functionality of any one or all of the logic components. In other embodiments, multiple chips can be used to separate the processing performed by any one of the logic components and the processor 106. Sensors 156 can communicate via a bus with the processor 106 and/or the logic components. The storage 108 is also in communication with the bus for providing storage of the motion data processed or tracked by the activity tracking device 100. Battery 154 is provided for providing power to the activity tracking device 100.

Figure 3:
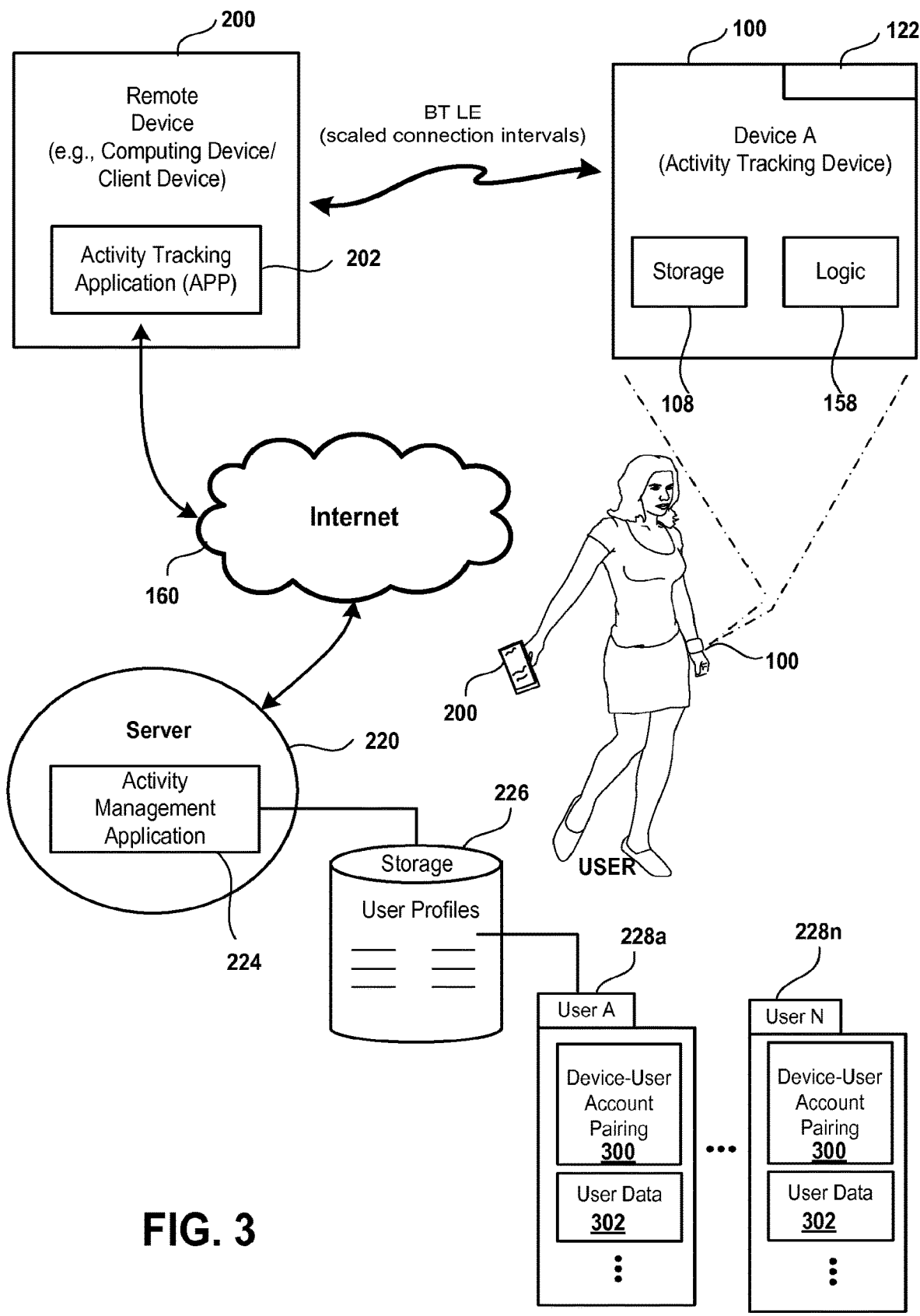
FIG. 3 illustrates an example of activity tracking device in communication with a remote device and interfaces with a server, in accordance with one embodiment of the present invention.

FIG. 3 illustrates an example of activity tracking device 100 in communication with a remote device 200. Remote device 200 is a computing device that is capable of communicating wirelessly with activity tracking device 100 and with the Internet 160. Remote device 200 can support installation and execution of applications (e.g., APPs, mobile APPs, etc.). Such applications can include an activity tracking application 202. Activity tracking application 202 can be downloaded from a server. The server can be a specialized server or a server that provides applications to devices, such as an application store. Once the activity tracking application 202 is installed in the remote device 200, the remote device 200 can communicate or be set to communicate with activity tracking device 100 (Device A). The remote device 200 can be a smartphone, a handheld computer, a tablet computer, a laptop computer, a desktop computer, or any other computing device capable of wirelessly interfacing with Device A. In one embodiment, the remote device can also have circuitry and logic for communicating with the Internet. However, it should be understood that an Internet connection is not required to enable the remote device 200 to communicate with the activity tracking device 100.

In one embodiment, remote device 200 communicates with activity tracking device 100 over a BLUETOOTH™ connection. In one embodiment, the BLUETOOTH™ connection is a low energy BLUETOOTH™ connection (e.g., BLUETOOTH™ LE, BLE, or BLUETOOTH™ Smart). Low energy BLUETOOTH™ is configured for providing low power consumption relative to standard BLUETOOTH™ circuitry. Low energy BLUETOOTH™ uses, in one embodiment, a 2.4 GHz radio frequency, which allows for dual mode devices to share a single radio antenna. In one embodiment, low energy BLUETOOTH™ connections can function at distances up to 50 meters, with over the air data rates ranging between 1-3 megabits (Mb) per second. In one embodiment, a proximity distance for communication can be defined by the particular wireless link, and is not tied to any specific standard. It should be understood that the proximity distance limitation will change in accordance with changes to existing standards and in view of future standards and/or circuitry and capabilities.

Remote device 200 can also communicate with the Internet 160 using an Internet connection. The Internet connection of the remote device 200 can include cellular connections, wireless connections such as Wi-Fi™, and combinations thereof (such as connections to switches between different types of connection links). The remote device, as mentioned above, can be a smartphone or tablet computer, or any other type of computing device having access to the Internet and with capabilities for communicating with the activity tracking device 100.

In one embodiment, a server 220 is also provided, which is interfaced with the Internet 160. The server 220 can include a number of applications that service the activity tracking device 100, and the associated users of the activity tracking device 100 by way of user accounts. For example, the server 220 can include an activity management application 224. The activity management application 224 can include logic for providing access to various devices 100, which are associated with user accounts managed by server 220. Server 220 can include storage 226 that includes various user profiles associated with the various user accounts. The user account 228a for user A and the user account 228n for user N are shown to include various information.

The information can include, without limitation, device-user account paring 300, system configurations, user configurations, settings and data, etc. The storage 226 will include any number of user profiles, depending on the number of registered users having user accounts for their respective activity tracking devices. It should also be noted that a single user account can have various or multiple devices associated therewith, and the multiple devices can be individually customized, managed and accessed by a user. In one embodiment, the server 220 provides access to a user to view the user data 302 associated with activity tracking device. The user data can include historical activity data.

The data viewable by the user includes the tracked motion data, which is processed to identify a plurality of metrics associated with the motion data. The metrics are shown in various graphical user interfaces of a website enabled by the server 220. The website can include various pages with graphical user interfaces for rendering and displaying the various metrics for view by the user associated with the user account. In one embodiment, the website can also include interfaces that allow for data entry and configuration by the user.

The configurations may include defining which metrics will be displayed on the activity tracking device 100. In addition, the configurations can include identification of which metrics will be a first metric to be displayed on the activity tracking device. The first metric to be displayed by the activity tracking device can be in response to a user input at the activity tracked device 100. As noted above, the user input can be by way of physical contact. The physical contact is qualified by the processor and/or logic of the activity tracking device 100 to determine if the physical contact should be treated as an input. The input can trigger or cause the display screen of the activity tracking device 100 to be turned on to display a specific metric, that is selected by the user as the first metric to display. In another embodiment, the first metric displayed in response to the input can be predefined by the system as a default.

The configuration provided by the user by way of the server 220 and the activity management application 224 can also be provided by way of the activity tracking application 202 of the computing device 200. For example, the activity tracking application 202 can include a plurality of screens that also display metrics associated with the captured motion data of the activity tracking device 100. The activity tracking application 202 can also allow for user input and configuration at various graphical user interface screens to set and define which input will produce display.

Figures 4A, 4B:
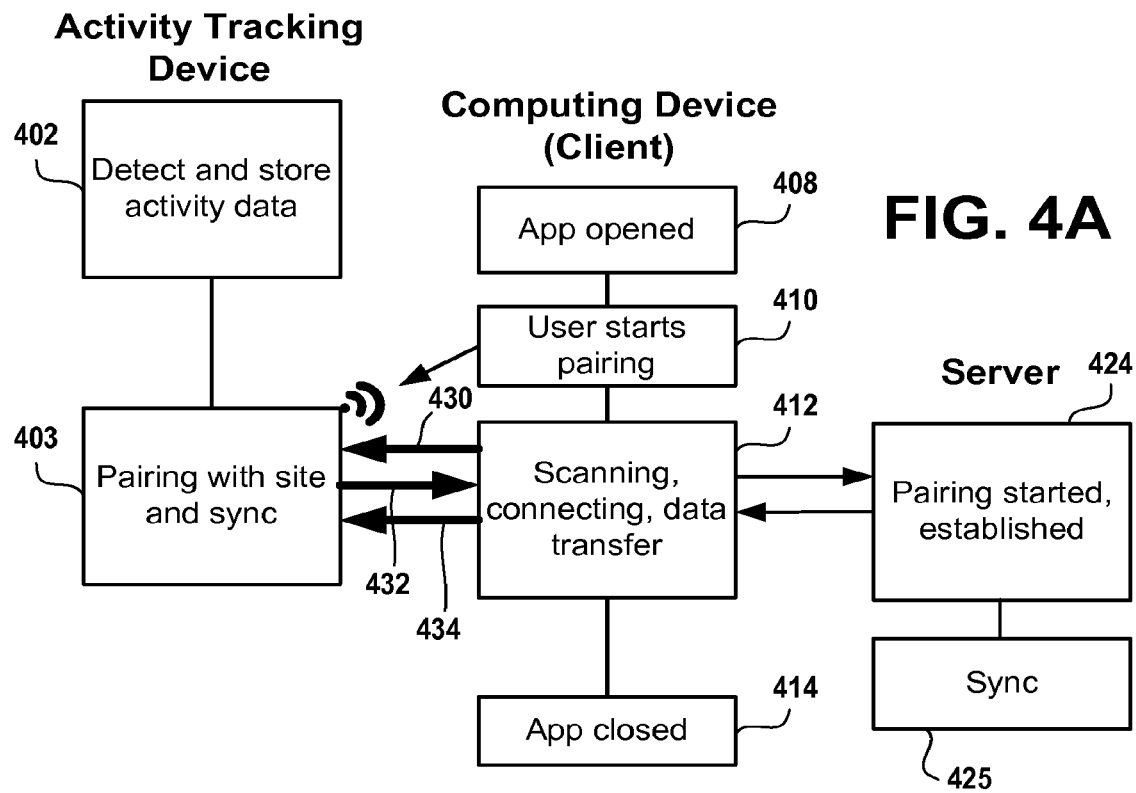
FIGS. 4A-4C illustrate embodiments for communication operations between an activity tracking device, a client device, and a backend server.
Figure 4C:
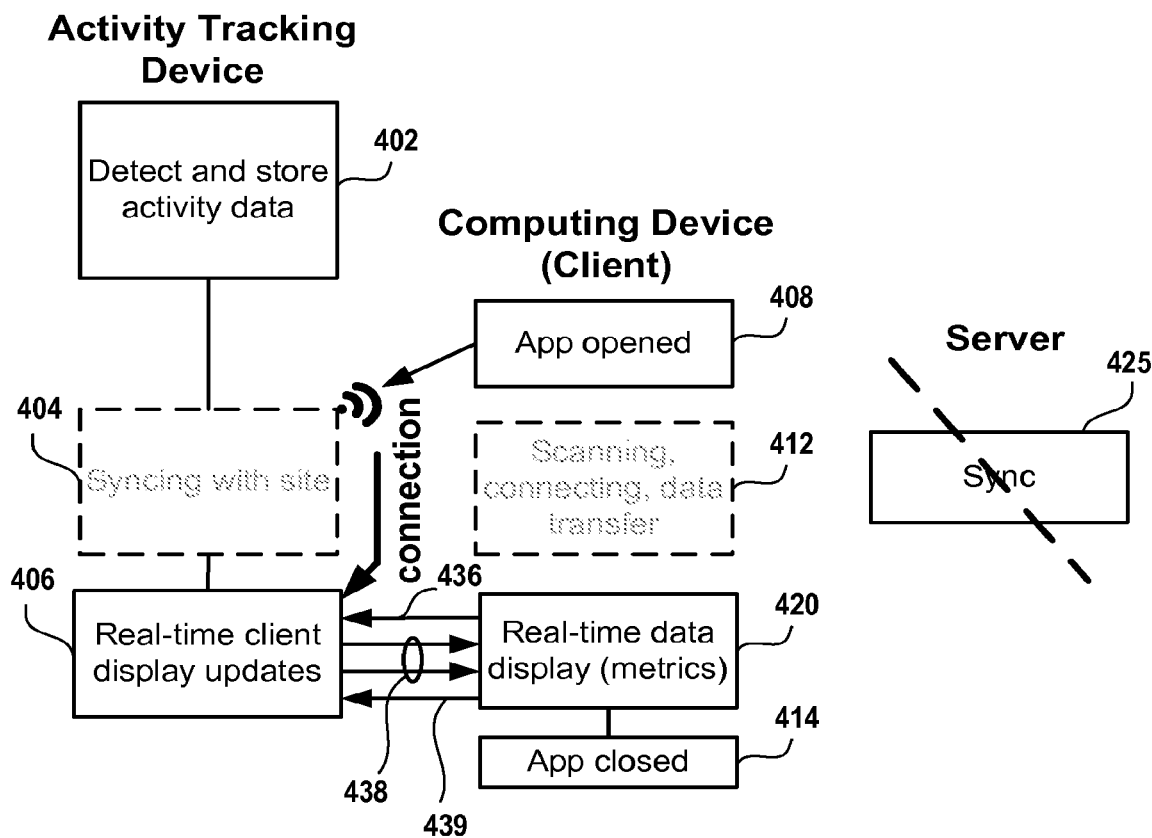

FIGS. 4A-4C illustrates embodiments of communication operations between an activity tracking device, a client device, and a backend server, in accordance with one embodiment of the present invention.

The communication described with reference to the flow diagrams in FIGS. 4A-4C should only be viewed as exemplary of operations that occur between the activity tracking device, a client device (computing device), and a backend server (server). In this illustrated example, thick pointed arrows indicate that a connection interval has been scaled up so as to operate data transfers at a first data transfer rate, while a thin pointed arrow indicates a connection interval that has been scaled down so as to operate data transfers at a second data transfer rate.

In one embodiment, the first transfer rate is designed to allow the transfer of larger amounts of data that have been stored on the activity tracking device over a period of time, such as since the last connection was made to a computing device. The activity tracking data stored on the activity tracking device can include, for example, motion data associated with the various activities performed by a user, data sensed by the activity tracking device, or data measured by the activity tracking device.

The various activities may include, without limitation, walking, running, jogging, walking up and down stairs, and general movement. Other information that can be stored by the activity tracking device can include, for example, measured information such as heart rate information, temperature information, etc. In one embodiment, storage of the activity tracking device will store this information for a period of time until a connection is made to a client device, such as a computing device configured to sync with the activity tracking device. In one embodiment, the computing device (client device) can be a smart phone, a tablet computer, a laptop computer, a desktop computer, or a general computing device.

In one embodiment, the first transfer rate is defined by scaling up the connection interval of the communication channel established between the activity tracking device and the client device. For example, if the communication channel is a low energy BLUETOOTH™ connection, the connection interval can be scaled to enable a transfer of packets that is more frequent than the second transfer rate.

First Transfer Rate (Connection Interval Scale-Up)

The connection interval for the first transfer rate can be scaled up to set a throughput of packets, such that each packet is transferred in less than about 200 milliseconds (ms). In one example embodiment, the first transfer rate is set to transfer one packet every about 10 ms to about 30 ms. In another example embodiment, the first transfer rate can be one packet every about 20 ms. In one embodiment, each packet is about 20 bytes.

In one embodiment, the first data transfer rate may be defined in terms of a frequency, in a range of between about 500 Bps (bytes per second) and about 2 kBps (kilobytes per second). In one example data transfer rate is about 1 kBps (kilobyte per second).

Second Transfer Rate (Connection Interval Scale-Down)

The connection interval for the second transfer rate can scaled down to set a throughput of packets, such that each packet is transferred at an interval that is greater than about 200 milliseconds (ms). In one example embodiment, the second transfer rate is set to transfer a packet every 500 ms. In some embodiments, depending on the frequency of events or lack of events, the transfer rate can be set to update only after several seconds (e.g., about 1-10 seconds). In one embodiment, each packet is about 20 bytes.

In one embodiment, the second data transfer rate may define a frequency value that is less than 500 bps (bytes per second). In another embodiment, the second data transfer rate can be set to a value that is less than 100 bps (bytes per second). In still another example, the second data transfer rate can be about 1 Bps (1 byte per second). In some embodiments, depending on the frequency of events or lack of events, the transfer rate can be scaled down even further.

It should be understood that these example rates, parameters, and/or sizes can change over time, depending on standards, customizations, and/or optimizations. So therefore, these parameters should only be viewed as examples. It is further understood that the methods and devices defined herein can implement embodiments that include more than two data transfer rates. In fact, the number of data transfer rates can include any number, based on a number of predefined scaled up or scaled down connection intervals. The number of intervals will vary, of course, depending on the implementation.

By scaling the connection intervals up or down, it is not the actual throughput that is being changed, but rather the possible bandwidth that can be supported by the channel. In the first data transfer rate, the scaled setting uses almost all of the channel bandwidth. In the second data transfer rate, most of the available channel bandwidth goes unused. A consideration for both transfer rates is latency, so the system does not want to have to wait too long before a single event (e.g., essentially one bit of information) can go from one device to another.

Returning to FIG. 4A, activity begins in operation 402 where the activity tracking device detects and stores activity data associated with motion or data collected by the device. In the example of FIG. 4A, it is assumed that the activity tracking device has never been synchronized a website (e.g., site) of a server. Therefore, a pairing of the activity tracking device to the site needs to occur, at least once 403.

The client device, in operation 408 may detect that an application is opened on the client device. The application that is opened is the activity tracking application 202, for example. In operation 410, the client device begins to pair with the activity tracking device 403. Pairing may occur, for example, upon request of a user that initiates the pairing.

The pairing, in this embodiment is a pairing between the activity tracking device and the site, which is enabled via the computing device client. For example, the scanning, connecting and data transfer at the computing device will enable the pairing with the site. If the activity tracking device has activity data, it will also be synchronized with the site, as shown in 424 and 425. The communication between the computing device and the activity tracking device is carried out in accordance with the first transfer rate, which uses a scaled-up connection interval to transfer data. The first transfer rate can include, for example, command data 430 requesting data from the activity tracking device, sending data 432, and acknowledgement information 434 for received data. At this point, the user may wish to close application 414 at the client computing device.

In FIG. 4B, an example is shown of a connection where the activity tracking device had previously been paired to the site on the server, in accordance with one embodiment of the present invention. In operation 402, activity data is detected and stored on the activity tracking device. At some point, an application is opened 408 at the computing device. As noted above, the application may be an activity tracking application 202. An update condition is detected by the client device, which is identified by opening the application. The update condition will act to scale-up the connection interval, so as to set a first data transfer rate.

The thick arrows 430, 432 and 434 represent the first data transfer rate, which is a faster transfer rate than the second transfer rate. Once the syncing with the site 404 and sync 425 is complete, using the scanning, connecting and data transfer 412 of the client, the operation of real-time client display updates 406 is processed.

The update condition has now changed, which causes a scale down of the connection intervals between the activity tracking device and the computing device. This, as noted above, causes the second transfer rate to govern for data exchanged to the computing device for real-time data display. In one embodiment, arrow 436 indicates a request from the computing device for real time updates 420. Arrows 438 indicate data transfers of any data available for transfer, using the second data transfer rate. Arrow 439 indicate a command that the client device has closed the application 414, so that the device can stop sending updates.

FIG. 4C illustrates an embodiment where the activity tracking device is connected to the computing device, without a connection with the server. Without server connection, the computing device (client) will not establish a pairing with the server, but instead will only establish a connection with the activity tracking device to perform real-time client display updates. As noted above, the activity tracking device will be set to communicate with the computing device using the second transfer rate, which is a result of scaling down the connection interval for performing the transfer of updates.

In this embodiment, the transfer of updates takes place to the computing device, which can display updates from the tracker in substantial real time. In one embodiment, the updates are transferred at a rate that is substantially not noticeable to a user viewing a changing screen or display of the computing device (e.g., the display of a smartphone, a smart watch, glasses device, etc.). In one example, the substantial real-time updates occur with transfer delay to the display that is less than about 2 seconds. In other embodiments, the transfer delay is less than about 1 second. In still other embodiments, the transfer delay is less than about 0.6 second. To human perception, the updates would appear to occur in real-time, wherein the updated activity data is continuously updated to the client device, and the display changes continuously or intermittently, depending on whether activity was captured or not. In some embodiments, the real time display will show numbers on a screen changing, such as counting steps, counting stairs, showing distance traveled, etc.

The communication between the client device and the server is executed using an Internet connection link, such as a Wi-Fi™ connection or cellular connection. As noted in this disclosure, the activity tracking device can be a wearable device on the wrist of a user, or a device that can be held by the user or attached to the user's clothing. As the user engages in motion or activities, the captured information can be transferred directly to the client device, such as a smart phone having an activity tracking application 202.

If the activity tracking application 202 is open, and the user is viewing one or more screens or data provided by the activity tracking application, that motion or activity data is transferred to the smart phone for display. Thus, if the user is currently viewing a screen that displays metric data associated with the activity being performed by the user, that activity can be updated substantially in real time as the user engages in the activity. For example, if the user is walking while viewing the screen that displays the number of steps, the number of steps can be shown to increase as the user is walking and viewing the display on the smart phone.

As the flow diagrams of FIGS. 4A-4C show, communication is managed between activity tracking device, the computing device, and the backend server. However, it should be understood that the communication between the activity tracking device and the client device can occur without having any Internet connection or connections to the backend server, as noted with response to FIG. 4C. When Internet connection is established by the client device at some point, the client device can then synchronize with the backend server, such as during background syncs, or when the app on the client device is again opened.

Figure 5:
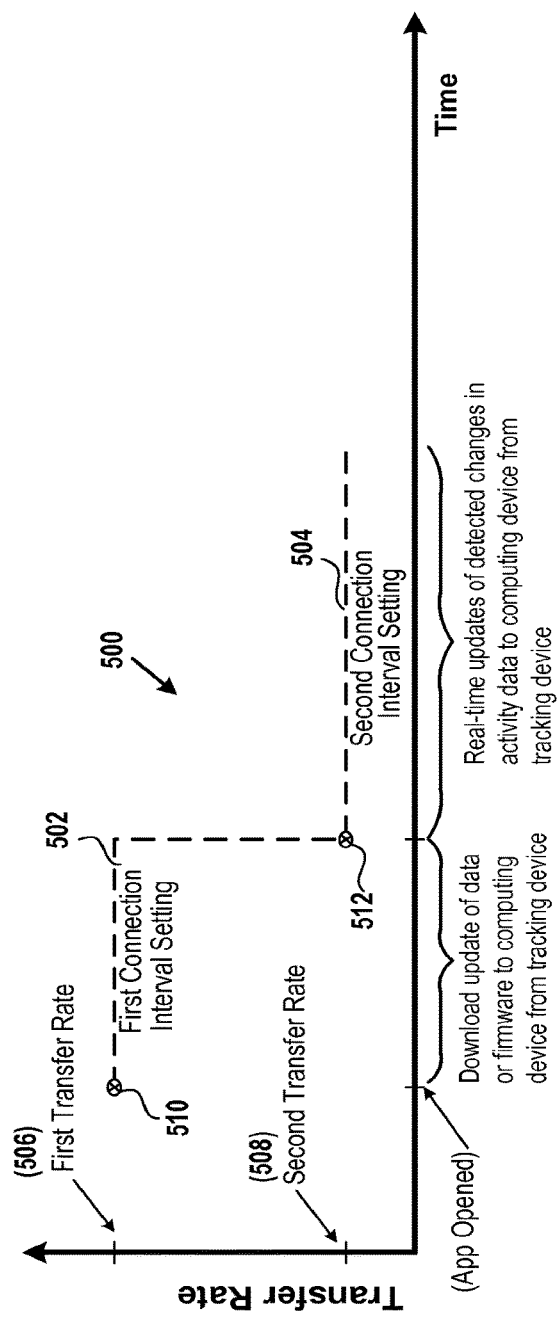
FIG. 5 is a diagram showing dynamic switching between first connection interval settings and second connection interval settings, in accordance with one embodiment of the present invention.

FIG. 5 is a diagram 500 illustrating the dynamic switching between first connection interval settings 502 and second connection interval settings 504, in accordance with one embodiment of the present invention. In this example, the vertical axis is the transfer rate, while the horizontal axis is time. At some point in time, an application is opened at a client device at 510. The application that is opened is, in one example, an activity tracking application 202, as described in FIG. 3. When the activity tracking application 202 is opened, the communication between activity tracking device and the client device will be scaled up in terms of the connection interval. The connection interval defines a first transfer rate 506 where packets are sent during a period of time, or the frequency.

As mentioned above, the first connection interval setting 502 may transfer one packet every about 10 ms to about 30 ms. The packet transfer occurs over a low-energy BLUETOOTH™ connection, which saves energy by the activity tracking device. In one embodiment, the first connection interval setting 502 will remain during the data transfer. The data transfer that occurs upon first opening the application 202 is to transfer data that has been stored in the activity tracking device for some time. This data may include data held by the activity tracking device for several hours, days, or even months.

Therefore, during the first connection interval setting 502, such collected and stored data is downloaded to the client device so as to enable the client device to process the data and display information on one or more graphical user interfaces of the activity tracking application 202. In one embodiment, the first connection interval setting 502 can also be used to transfer firmware from the client device to the activity tracking device.

The transfer of firmware to the activity tracking device generally includes transferring a larger chunk of data, and the increased or scaled up connection interval allows for such transfer to occur at a relatively fast rate. By using a scaled up connection interval, over a BLUETOOTH™ low-energy connection, the scaled-up connection interval provides for essentially a serialized transmission channel between the client device and the activity tracking device. In BLUETOOTH™ low-energy, serial data transfers are not allowed, but by scaling up the connection interval, it is possible to simulate an actual serial connection. In the context of firmware updates, it is noted that the firmware image is running on the activity tracking device, so updates need to be coordinated with the transmission of commands to save state, stop running the image, install the image, and resume execution of the firmware image update. Because the connection between the activity tracking device and the client devices is essentially serialized (due to the scaled up connection interval setting), the firmware image files and commands to update can be managed by the server.

The server, when it is determined that updates are needed, can issue instructions to scale up the connection interval, transfer the firmware updates and coordinate the install, directly from the server. In one embodiment, by coordinating the firmware update from the server, it is not necessary to have the application running on the client device manage the updates, which also avoids having to coordinate with App stores and sites to enable firmware updates. The determination to update, the updating, and the coordination of the updates can be directed from the server, at any schedule or when updates are needed. In this configuration, the client device simply acts as a communication pipe that enables the direct communication and exchange of control and data/firmware to the activity tracking device from the server.

In one embodiment, a device 100 can have two operating systems (OSs) so that each can be updated independently, and without risk of leaving device unable to communicate over BLUETOOTH™. In one configuration, the firmware update protocol includes deciding which OS the tracker will boot. The site on the server stores information about every firmware version and can compute deltas and data migration instructions from any version to any other version. For example, the computing device client can iteratively query current state from device 100, send the state to the site, receives in response a particular command to send to the device, and then after executing the command again queries the device for its current state. In this manner, no details about any particular version needs to be known by the client, as the site can manage the firmware updates.

Continuing with FIG. 5, at point 512, it is detected that the download of data has concluded or the firmware update has concluded, and at that point the connection interval is scaled down to a second connection interval setting 504. The second connection interval setting 504 acts to reduce the transfer rate to a second transfer rate. As noted above, the second transfer rate is used because the amount of data being transferred during this time only represents updates to data stored in the client device. For example, the updated data can include currently monitored step count, which is transferred as small packet updates to the client device.

The client device can then display in substantial real-time the updates on one or more of the graphical user interface screens provided by the activity tracking application 202. As noted above, one example of the second transfer rate can be to transfer one packet every 500 ms. This transfer rate is sufficient to update one or more of the metrics being captured by the activity tracking device and configured for display in substantial real-time on the client device (screen of a smart phone). The second connection interval setting 504 will remain during the period of time when updates for changes in activity data are captured by the activity tracking device or data is ready for transfer. When the activity tracking application 202 closes, the substantial real-time updates will stop or terminate.

Figure 6:
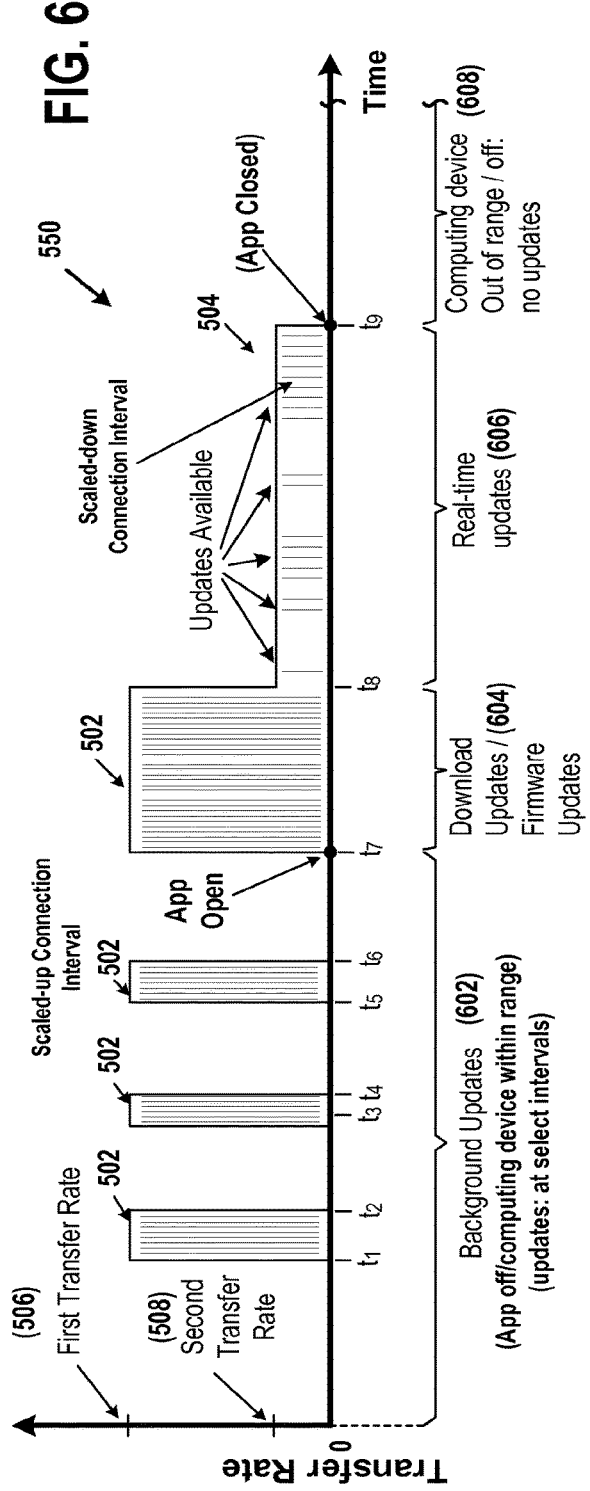
FIG. 6 illustrates a graph showing various periods of time when transfers may occur between the activity tracking device and the client device, in accordance with one embodiment of the present invention.

FIG. 6 illustrates a graph 550 showing various periods of time when transfers occur between the activity tracking device and the client device, in accordance with one embodiment of the present invention. In the example, data transfers (e.g., updates) occur during background updates 602, download updates 604, real-time updates 606, and no updates during out of range computing devices 608. In this example, the first transfer rate 506 and the second transfer rate 508 are shown in the vertical axis. The horizontal axis displays time.

When the activity tracking application 202 is not open, but the computing device is within a range of communication with the activity tracking device, background updates 602 are enabled. Background updates are programmed at predetermined times depending on how often or how infrequent updates have been received from an activity tracking device. In the graph, background updates occurred at times t1-t2, t3-t4, and t5-t6. In one embodiment, background syncing can be triggered by the tracker advertising that it has data to sync and typically the real world time between these data syncs is 15-90 minutes, or typically occurring in the 20-30 minute range. Background mode updates/syncing, however, is enabled when the activity tracking device is within communication range of the computing device (client device). In one embodiment, the range can be defined by capabilities of low-energy BLUETOOTH™ standards, and also taking into consideration the environment and/or structures between the tracker and the client.

In other embodiments, other communication distances may be enabled if other wireless standards are used now or in the future. As further shown, the background update 602, in one embodiment occur at the first transfer rate 502, which implement the first connection interval setting. In an alternate embodiment, the background update 602 can be performed using the second interval connection setting 504. Also when the app is closed, the connection may or may not be maintained. In other words, even when the app is closed, there may be a constant "Second Transfer Rate" connection that is scaled up to the "First Transfer Rate" at certain intervals in order to sync data. But it is also possible that there is no connection between the background data sync intervals. But in either case, the data sync may occur at the First Transfer Rate so that we keep the BTLE hardware in high power transmitting state for as short a time as possible.

Download updates 604 occur at the first connection interval setting, where larger chunks of data are transferred from storage of the activity tracking device when it is detected that the application has opened at time t7. Between time t7 and t8, the download updates 604 occur, or firmware updates to the activity tracking device.

The transfer rate is set at the first transfer rate by scaling up the connection interval between the activity tracking device and the computing device (transferring at the first connection interval setting 502). After it is detected that the application has closed at time t8, the second connection interval setting 504 is set by scaling down the connection interval. The scaling down can occur immediately or after some period of time, or based on a predefined state or condition. This places real-time updates 606 at the second transfer rate 508. As illustrated by the vertical bars, transfers are less continuous during this time, and depend on whether or not data is being produced by the activity tracking device and there is a need to transfer the data to the client device. For any such transfers of data, the transfers will occur at the second transfer rate, dictated by the second connection interval setting 504. At time t9, it is determined that the application has closed. If the computing device goes out of range of the activity tracking device, no updates will occur during time 608.

Figure 7:
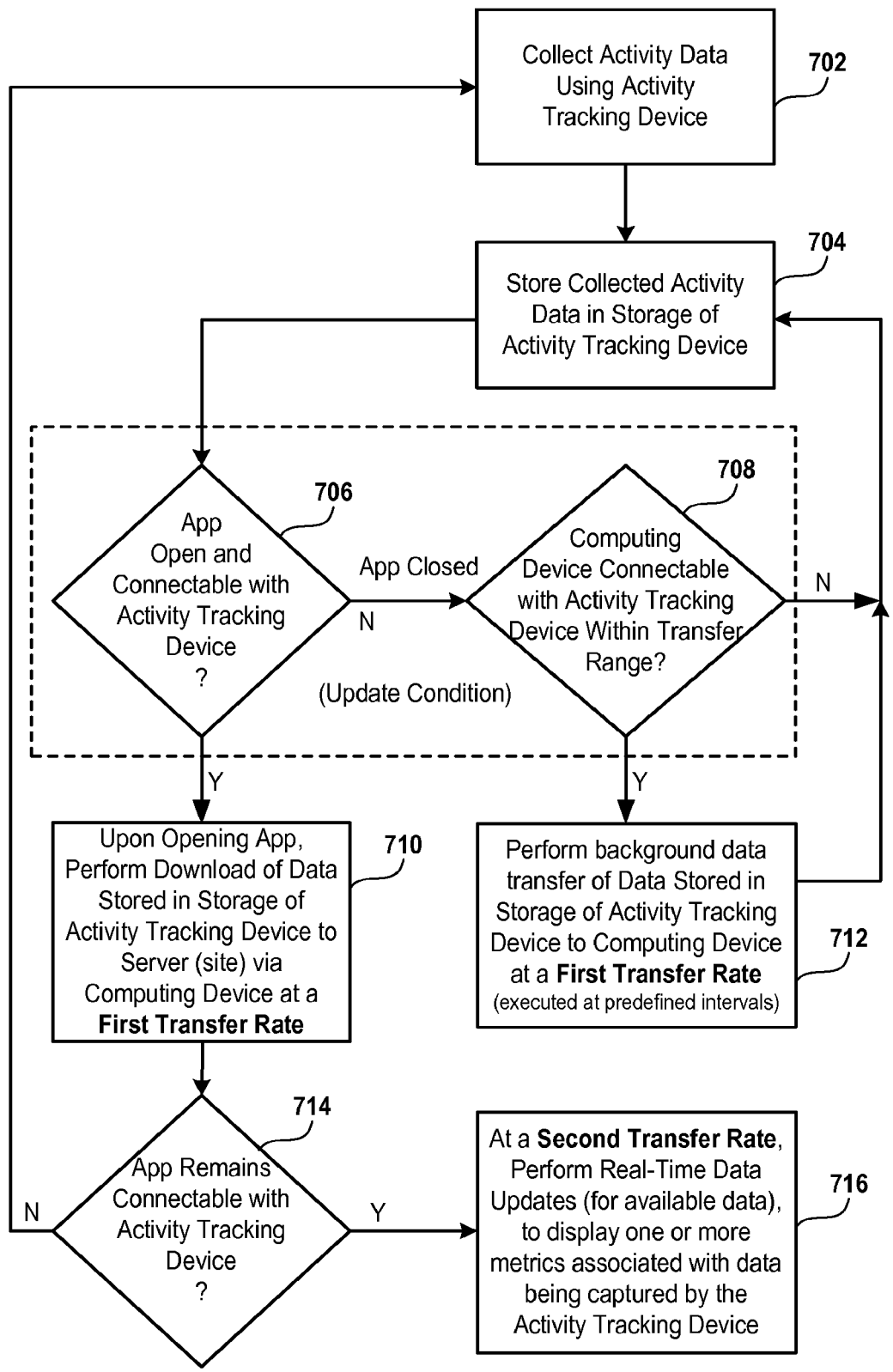
FIG. 7 illustrates a flowchart diagram associated with one embodiment of the present invention where the connection interval is scaled up or down depending on update condition detected between the activity tracking device and the computing device (client device).

FIG. 7 illustrates a flowchart diagram associated with one embodiment of the present invention where the connection interval is scaled up or down depending on update condition detected between the activity tracking device and the computing device (client device). The method begins in operation 702 where activity data is collected using the activity tracking device. The activity data is a result of motion data produced by the user who is wearing, holding, or carrying connectivity tracking device. The activity data can also be associated with data monitored by the device, such as blood pressure, heart rate, barometer reading, and other metrics associated with environmental conditions or conditions of a user. In operation 704, the collected activity data is stored in storage of the activity tracking device. The storage can be any type of memory, such as nonvolatile memory.

The update condition is determined at operation 706 and 708, in one example. For instance, in operation 706 it is determined if the application (e.g., activity tracking application 202) is open and is connectable (e.g., within range for connection) with the activity tracking device. If the application is not opened, it is determined in operation 708 if the computing device is connectable with the device within a transfer range. If the computing devices is within a transfer range, the method moves to operation 712. In operation 712, a background data transfers performed to the computing device using the first transfer rate, which is at a pre-defined scaled interval connection speed.

In another embodiment, background transfers can be executed at the second transfer rate. If it is determined that the device is not within the range of transfer with the computing device in operation 708, the method returns to operation 702 where that activity tracking device continues to collect data. If it is determined in operation 706 that the application is open and is within the transfer range, the method moves to operation 710 where a download of data stored in the storage of the activity tracking device is transferred to the computing device at the first transfer rate. As noted above, the first transfer rate is faster than the second transfer rate, and is designed to transfer larger amounts of data over a low-energy BLUETOOTH™ wireless connection.

The first transfer rate may be, for example, enabling the transfer of a packet every 10 ms to 30 ms, whereas the second transfer rate may be enabling transfer of a packet after more than 200 ms, or after more than 300ms, or after 400ms, or after 500 ms. In operation 714, it is determined that the application is connected with the activity tracking device and is open. If the application remains open, then real-time updates 716 are performed such that one or more metrics associated with collected activity data is transferred to the computing device from the activity tracking device. This information can be displayed in substantial real time on one or more screens of the activity tracking application 202 rendered on a computing device 200 (e.g. smart phone, tablet, etc.). If in operation 714 it is determined that the application is no longer open, the method would return back to 702 where the activity tracking device continues to track data and store it in operation 704.

Figure 8:
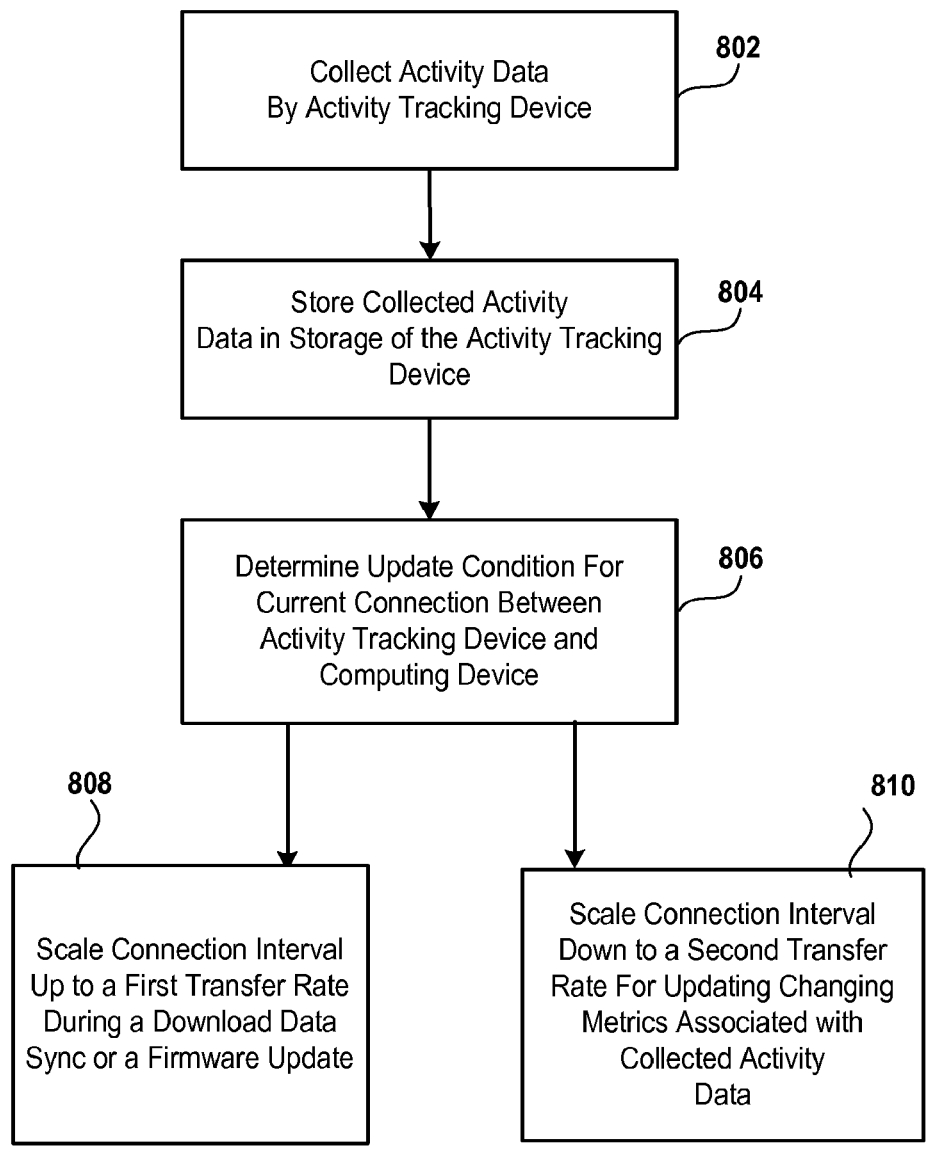
FIG. 8 illustrates a flowchart diagram of one embodiment of the present invention.

FIG. 8 illustrates a flowchart diagram of one embodiment of the present invention. In this example, operation 802 includes collecting activity data by the activity tracking device. As noted above, the type of data collected by the activity tracking device can be associated with motion data, data monitored from the user, data monitored from surrounding conditions, etc. In operation 804, the collected activity data is stored in storage of the activity tracking device.

In operation 806, the update condition is determined for a current connection between the activity tracking device and a computing device. The update condition can identify whether an application has just been opened, whether the application remains open after a first transfer rate has concluded to transfer stored data or perform firmware updates, or if background updates are required. Depending on the update condition, it is determined whether to scale the connection interval up or down to optimize the data transfer operation. In operation 808 it is determined that the connection interval should be scaled up to a first transfer rate during a download of data from the activity tracking device to the client device, or a firmware update from the client device to the activity tracking device.

In operation 810, it is determined that the connection interval should be scaled down to a second transfer rate for updating changes to metrics associated with collected activity data. At the scaled down connection interval rate, e.g., the second transfer rate, updates associated with one or more metrics can be transferred to the client device for display on one or more graphical user interface screens. The graphical user interface screens can include metric data that is changing on the fly as the user generates activity.

For instance, if the user is walking while viewing the one or more graphical user interface screens of the client device (e.g. running the activity tracking application 202), the step count will be shown to be increasing as the user takes each step. In another example, if the user is climbing stairs, the stair account would be increasing. In still another example, if the user is producing very active motion, the count of very active minutes can be shown to increase dynamically. Similarly, the calories burned count can be shown to increase dynamically while the user is performing an activity.

In one embodiment, synchronization (e.g., syncing) is a process between an activity tracking device and the web site. For example, the client device can be viewed as a dumb pipe that merely transmits data to the web site and then transmits a response to the activity tracking device. If there is no internet connection for the client device, no syncing is performed with the website. Syncing can then occur at a later time when an Internet connection has been established. In one embodiment, a "store and forward" type of approach can be implemented which just introduces asynchronous delays. The client would retrieve data from the tracker when it could, store it, and then relay the data to the site and get a response from the site later when there was an internet connection. In one embodiment, later, when the tracker was again available, the client could send the stored response to the tracker.

Figure 9:
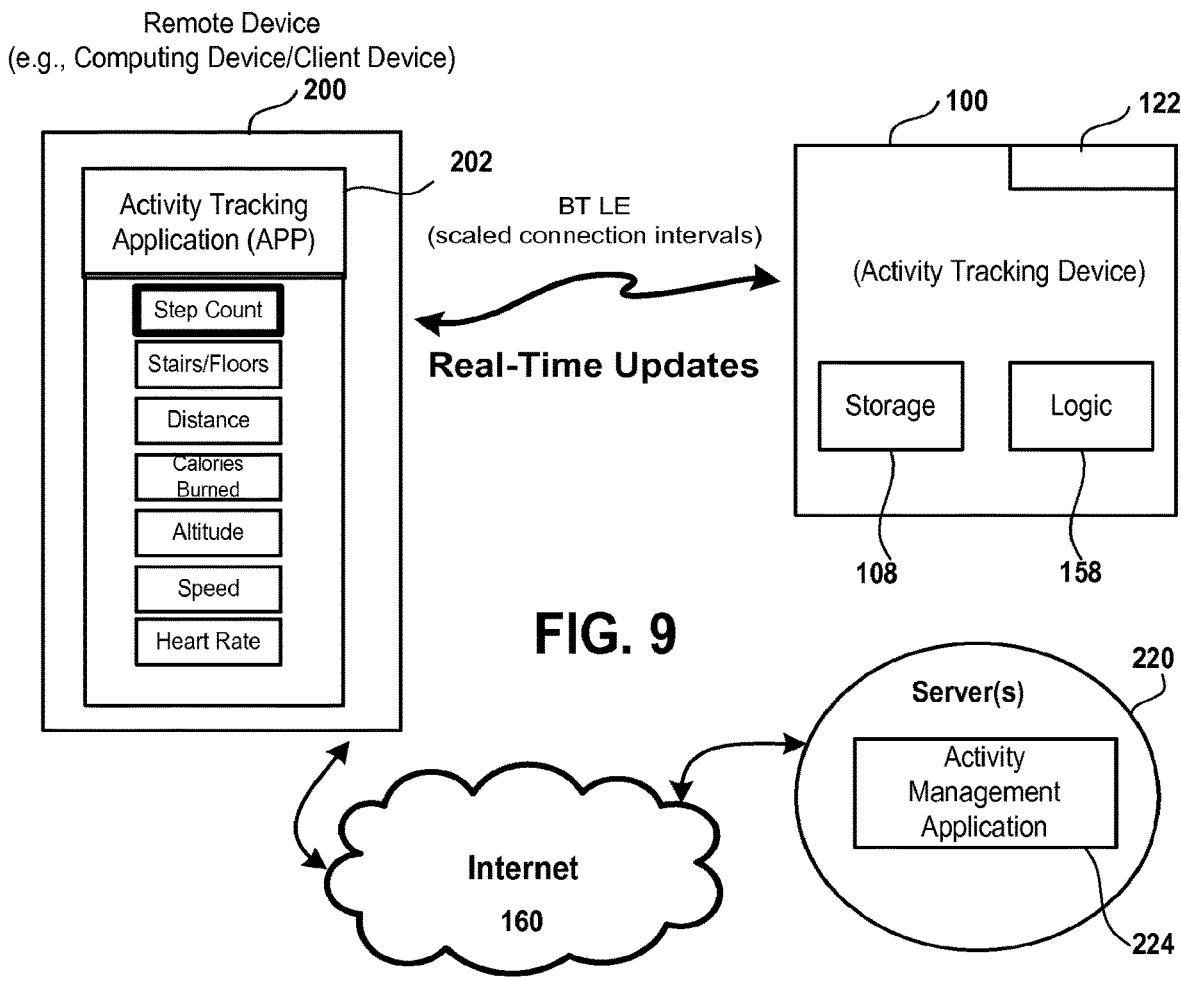
FIG. 9 illustrates an example where the computing device is in communication with device, in accordance with one embodiment of the present invention.

FIG. 9 illustrates an example where the computing device 200 is in communication with device 100, in accordance with one embodiment of the present invention. In this example, the computing device 200 is shown to be executing an activity tracking application 202. Although activity tracking application 202 can include any number of screens, icons, pages, navigational features, graphics, etc., several metrics are shown for ease of discussion.

The metrics include, for example, step count, stairs or floors ascended or descended, distance traveled, calories burned, altitude measurements, speed information, heart rate information, and other metrics that may be measured, calculated, monitored, obtained, or captured. As noted above, the computing device 200 is capable, in one embodiment, to communicate with the Internet 160. Servers 220 are made accessible over the Internet, which can provide access to an activity management application 224.

In one embodiment, real-time updates between the computing device 200 and the activity tracking device 100 can occur without Internet connection. As noted above, communication to provide real-time updates may occur utilizing a second data transfer rate. The second data transfer rate is set based on a scaling down of the connection interval between the computing device 200 and the activity tracking device 100. The second data transfer rate is sufficient to provide information to the computing device from the activity tracking device 100, and computing device 200 to display the changing information on a screen.

The changing information can be represented as numerically increasing data that changes as the motion data/activity data from the activity tracking device 100 changes. In some embodiments, it is not necessary that the data be numerically increasing, so long as some change or update is generated, shown, or displayed. Therefore, the numerical changes on the display will appear to the user to be occurring in substantial real-time. As noted above, substantial real-time may include a slight delay, such as less than 2 seconds, less than 1 second, or less than a fraction of a second. The delay, in one embodiment is configured to be less than what would be normally perceived by a human to be delayed data. Thus, the screen output changes as the motion produced by that activity tracking device 100 changes.

Figure 10A:
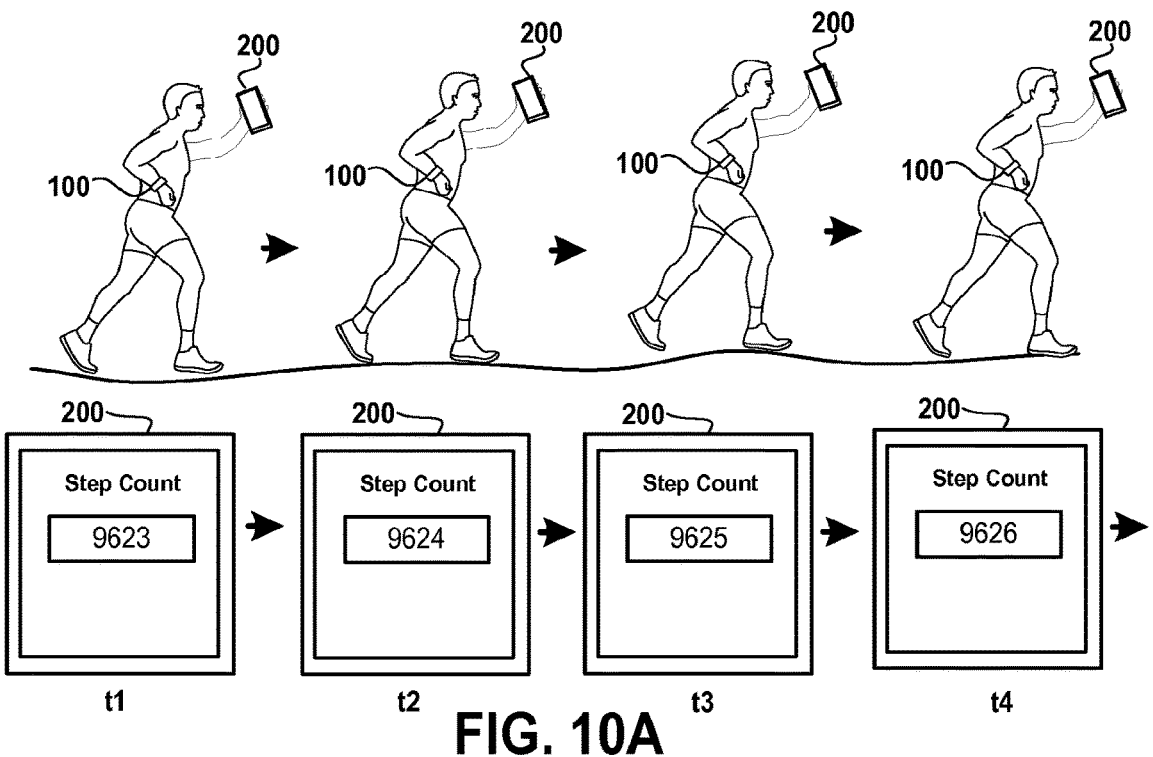
FIG. 10A illustrates an example of a user wearing an activity tracking device on his wrist, and having access to a computing device.

FIG. 10A illustrates an example of a user wearing an activity tracking device 100 on his wrist, and having access to a computing device 200. While the user walks, jogs, or runs, the user is able to view the activity captured by the activity tracking device 100 on the display screen of the computing device 200. As illustrated, the user may have selected a screen of the activity tracking application 202, where step count is displayed.

At time t1, the step count is shown to be 9623, at time t2, the step count is shown to be 9624, at time t3, the step count is shown to be 9625, at time t4, the step count is shown to be 9626. The display of step count, in this example, will continue to numerically increase as the user continues to engage in motion that can be categorized as step count. The motion categorized as step count can include simple walking activity, jogging activity, writing activity, sprinting activity, or simple moving of the activity tracking device.

Figure 10B:
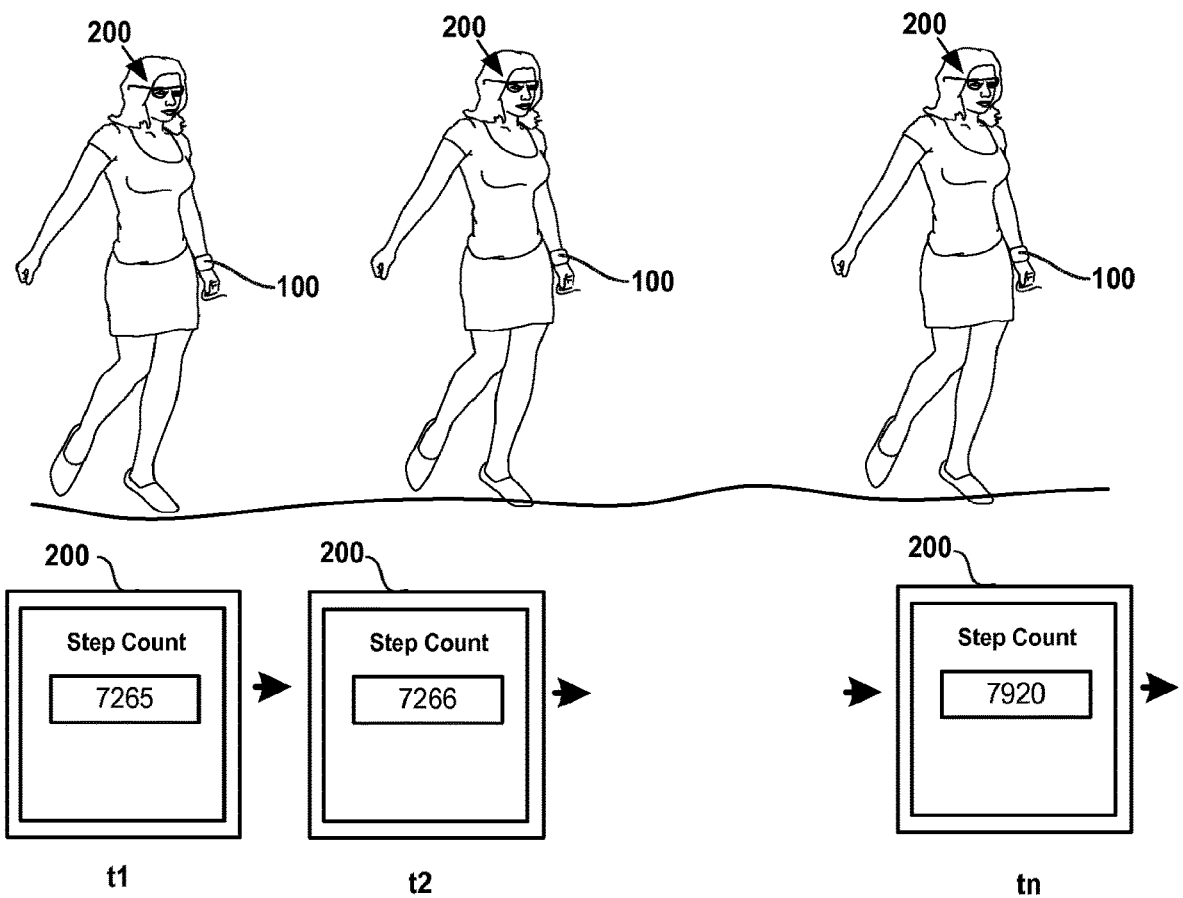
FIG. 10B illustrates an example where the user is wearing a computing device, in the form of computing glasses, in accordance with one embodiment of the present invention.

FIG. 10B illustrates an example where the user is wearing a computing device 200, in the form of computing glasses, in accordance with one embodiment of the present invention. In this example, the computing glasses are configured to include a screen that will display a selected metric. In this example, the selected metric is step count. Step count is shown to be changing from 7265, 7266, and then 7920, as time progresses and motion by the user continues to change. If the user stops walking or moving, the step count display will pause and hold the current step count without increasing. When the user resumes motion, the step count will then resume and numerically increase and/or change is state or update from the current or previous step count.

By communicating the step count to the users glasses, the information provided to the user can be monitored in substantial real-time as the user walks around or engages in activity. Providing information to the users glasses (which include a display coupled to a computing device, having wireless communication logic), also frees the user from having to hold a computing device in his or her hands. This may become more important when certain activities require the user to have full use of his or her hands, but still the user desires to see or understand the current physical activity and metrics associated with the physical activity as it changes. Certain activities can include, for example, running marathons, engaging in obstacle course running, bicycle riding, working in an office, walking in the park, walking at home, or any activity that requires the user to have freer use of his or her hands, but still providing the user real-time updates concerning the activity.

By way of this example, it should be understood that the activity tracking device 100 can be made to communicate with any number of devices. The devices can include, as mentioned above, smart phones, watch computers, glasses, wearable displays, tablet computers, touch base computers, desktop computers, etc.

Figure 11:
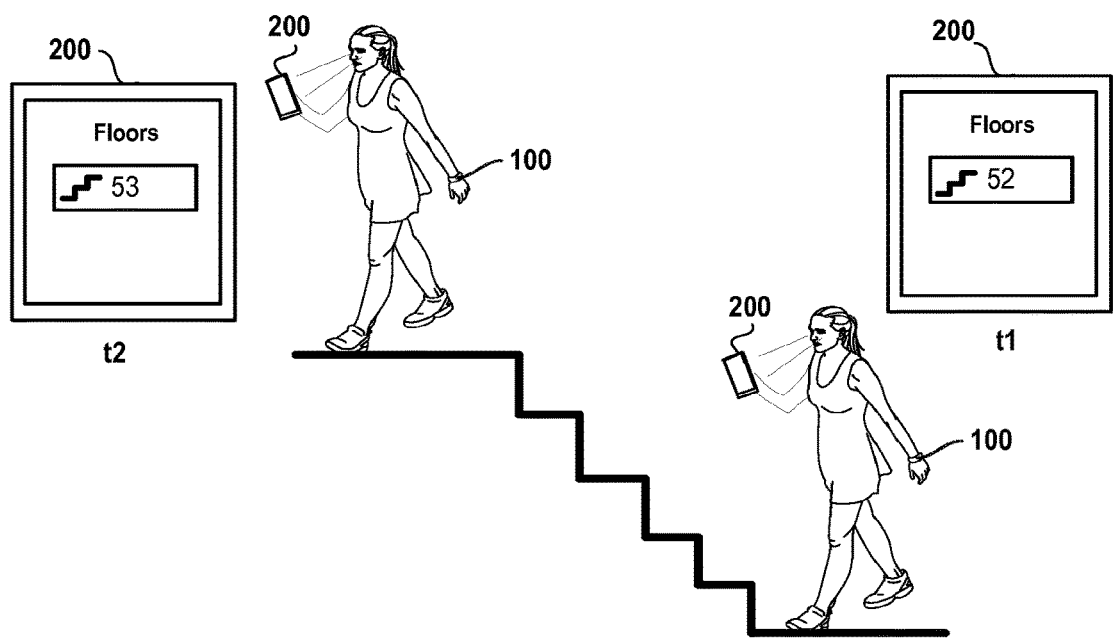
FIG. 11 illustrates an example where the user is climbing stairs, and is achieving floor count increases, in accordance with one embodiment of the present invention.

FIG. 11 illustrates an example where the user is climbing stairs, and is achieving floor count increases, in accordance with one embodiment of the present invention. In this example, the user has engaged in a number of floor ascending motions, which are displayed as 52 floors ascended at time t1. When the user climbs another floor, the floor metric will show 53 floors, on the screen of the computing device 200. The changes are dynamic and is in substantial real-time as the user continues to move from floor to floor. Although the measurement of floor count is occurring, step count is also concurrently being calculated (as well as all other metrics that can be calculated based on motion). If the activity tracking application 202 remains open, the user can navigate to another screen and view the step count, distance traveled, calories burned, altitude, speed, heart rate, or other metrics that may be changing (or had changed since the last view).

In some examples, a screen can provide metric information concerning a plurality of metrics. In that configuration, the real-time changes can be occurring to more than one metric at the same time. For instance, step count can be increasing at the same time as calorie increases change, and at the same time that distance changes. Therefore, any number of viewing configurations can be provided to a user, depending on the navigational screens provided by the activity tracking application 202.

Figure 12:
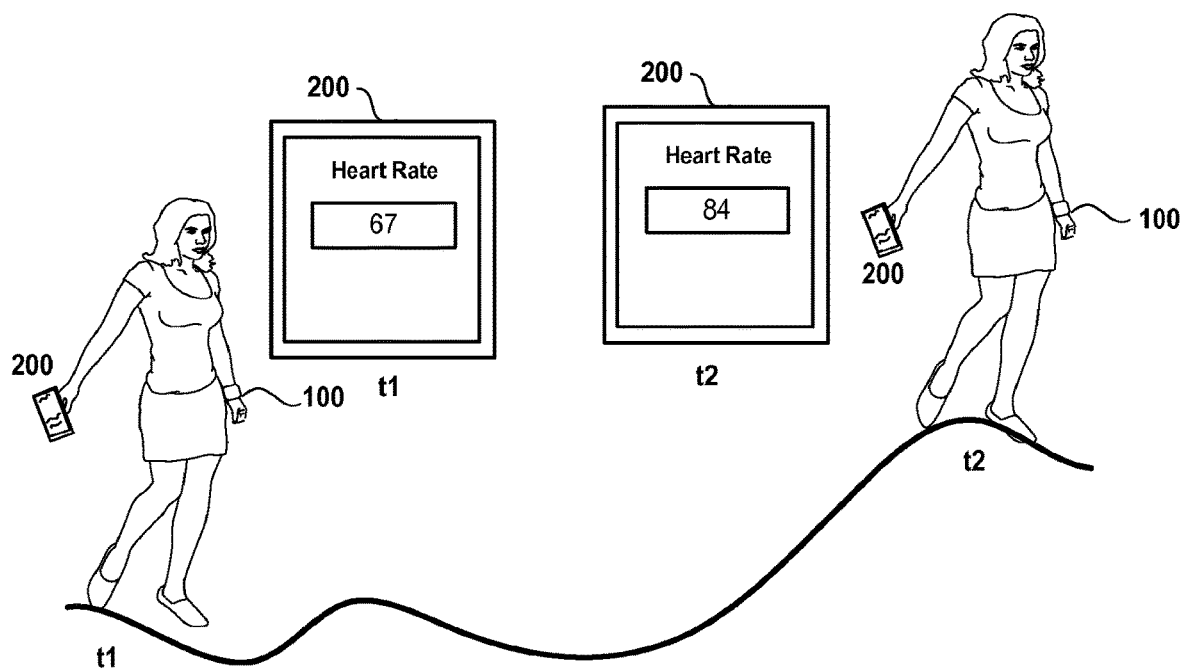
FIG. 12 illustrates yet another example where user is engaging in physical activity.

FIG. 12 illustrates yet another example where user is engaging in physical activity. The user at time t1, is shown to be walking while viewing the heart rate metric on the computing device 200. As the user continues to walk and exert physical energy, at time t2, the user's heart rate will show a real-time increase from 67 bpm (beats per minute) up to 84 bpm. Although only 67 bpm and 84 bpm are shown in the illustration, it should be understood that as the heart rate changed from 67 to 84, the substantial real-time display of the computing device 200 could have shown the progression increase up to 84 beats per minute.

In one embodiment, heart rate can be monitored by the activity tracking device 100 using various technologies. One technology can include using optical sensors that measure beats in a user's blood vessels, while the activity is occurring. The optical sensors can emit light toward a blood vessel, and then measure the reflections from the blood vessel. The reflections of light can then be processed to determine the beats per minute associated with the current monitoring. In one embodiment, the measurement of beats can occur at the wrist where the activity tracking device 100 is worn. In another embodiment, the user can place his or her finger over the activity tracking device 100 (e.g., over a sensing location), which would then allow the activity tracking device to measure beats from the users hand or fingers, and then produce the heart rate in beats per minute.

In some embodiments, a device is provided. The device is defined in a form of a wearable wrist attachable structure. In one embodiment, the device has a housing that is at least partially constructed or formed from a plastic material. In one embodiment, the housing of the device includes an altimeter. The defines can further include a transiently visible display, or a dead-front display, a touch screen display, a monochrome display, a digital display, a color display, or combination thereof.

In one example, the screen having dead front operation configures the screen to remain in an off-state until activated. In one embodiment, a dead front display is visible only when it needs to be lit. For instance, it can conceal an LED or a printed message on a display window, metric data, time of day, a warning light, a caution light, or data that may go unnoticed if the normal transparent LED were visible at all times. In one embodiment, a dead front display may blend in with the background of the device. Thus, dead fronting "cleans up" the appearance of the panel and avoids end user confusion during operation. Additionally, power savings are achieved, as the device is off/unlit when not in use or the user does not need information displayed and lit when activated by the user.

In yet another embodiment, the device can include one or more accelerometers. In one specific example, the device can include a 3-axis accelerometer. On still another embodiment, a 3-axis accelerometer can be replaced with or replicated by use of separate accelerometers (e.g., 3 accelerometers) positioned orthogonally to each other.

Figure 13:
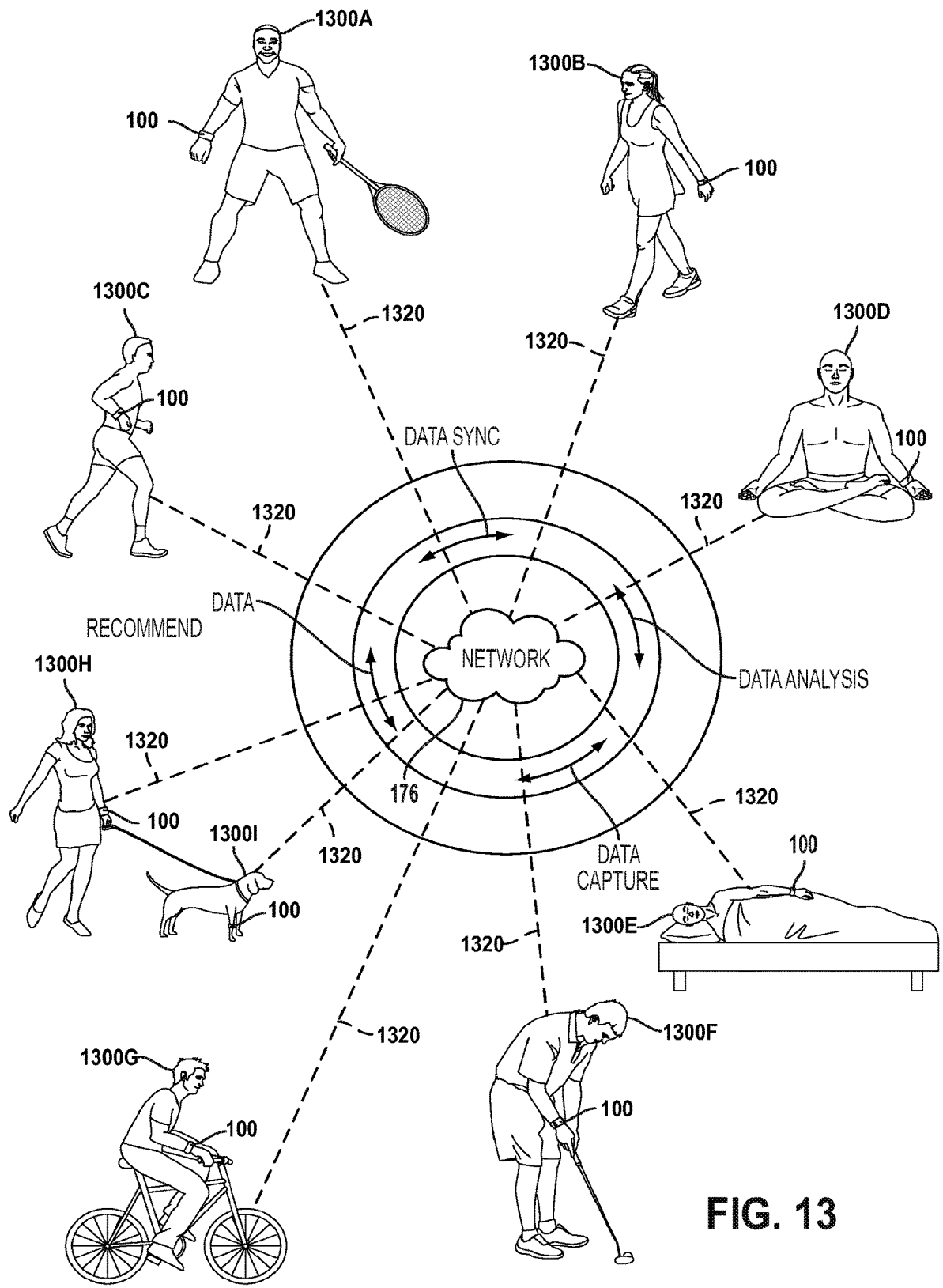
FIG. 13 illustrates an example where various types of activities of users can be captured or collected by activity tracking devices, in accordance with various embodiments of the present invention.

FIG. 13 illustrates an example where various types of activities of users 1300A-1300I can be captured by activity tracking devices 100, in accordance with one embodiment of the present invention. As shown, the various types of activities can generate different types of data that can be captured by the activity tracking device 100. The data, which can be represented as motion data (or processed motion data) can be transferred 1320 to a network 176 for processing and saving by a server, as described above. In one embodiment, the activity tracking device 100 can communicate to a device using a wireless connection, and the device is capable of communicating and synchronizing the captured data with an application running on the server. In one embodiment, an application running on a local device, such as a smart phone or tablet or smart watch can capture or receive data from the activity tracking device 100 and represent the tract motion data in a number of metrics.

In one embodiment, the device collects one or more types of physiological and/or environmental data from embedded sensors and/or external devices and communicates or relays such metric information to other devices, including devices capable of serving as Internet-accessible data sources, thus permitting the collected data to be viewed, for example, using a web browser or network-based application. For example, while the user is wearing an activity tracking device, the device may calculate and store the user's step count using one or more sensors. The device then transmits data representative of the user's step count to an account on a web service, computer, mobile phone, or health station where the data may be stored, processed, and visualized by the user. Indeed, the device may measure or calculate a plurality of other physiological metrics in addition to, or in place of, the user's step count.

Some physiological metrics include, but are not limited to, energy expenditure (for example, calorie burn), floors climbed and/or descended, heart rate, heart rate variability, heart rate recovery, location and/or heading (for example, through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality and/or duration, pH levels, hydration levels, and respiration rate. The device may also measure or calculate metrics related to the environment around the user such as barometric pressure, weather conditions (for example, temperature, humidity, pollen count, air quality, rain/snow conditions, wind speed), light exposure (for example, ambient light, UV light exposure, time and/or duration spent in darkness), noise exposure, radiation exposure, and magnetic field.

Still further, other metrics can include, without limitation, calories burned by a user, weight gained by a user, weight lost by a user, stairs ascended, e.g., climbed, etc., by a user, stairs descended by a user, steps taken by a user during walking or running, a number of rotations of a bicycle pedal rotated by a user, sedentary activity data, driving a vehicle, a number of golf swings taken by a user, a number of forehands of a sport played by a user, a number of backhands of a sport played by a user, or a combination thereof. In some embodiments, sedentary activity data is referred to herein as inactive activity data or as passive activity data. In some embodiments, when a user is not sedentary and is not sleeping, the user is active. In some embodiments, a user may stand on a monitoring device that determines a physiological parameter of the user. For example, a user stands on a scale that measures a weight, a body fat percentage, a biomass index, or a combination thereof, of the user.

Furthermore, the device or the system collating the data streams may calculate metrics derived from this data. For example, the device or system may calculate the user's stress and/or relaxation levels through a combination of heart rate variability, skin conduction, noise pollution, and sleep quality. In another example, the device or system may determine the efficacy of a medical intervention (for example, medication) through the combination of medication intake, sleep and/or activity data. In yet another example, the device or system may determine the efficacy of an allergy medication through the combination of pollen data, medication intake, sleep and/or activity data. These examples are provided for illustration only and are not intended to be limiting or exhaustive.

This information can be associated to the users account, which can be managed by an activity management application on the server. The activity management application can provide access to the users account and data saved thereon. The activity manager application running on the server can be in the form of a web application. The web application can provide access to a number of websites screens and pages that illustrate information regarding the metrics in various formats. This information can be viewed by the user, and synchronized with a computing device of the user, such as a smart phone.

In one embodiment, the data captured by the activity tracking device 100 is received by the computing device, and the data is synchronized with the activity measured application on the server. In this example, data viewable on the computing device (e.g. smart phone) using an activity tracking application (app) can be synchronized with the data present on the server, and associated with the user's account. In this way, information entered into the activity tracking application on the computing device can be synchronized with application illustrated in the various screens of the activity management application provided by the server on the website.

The user can therefore access the data associated with the user account using any device having access to the Internet. Data received by the network 176 can then be synchronized with the user's various devices, and analytics on the server can provide data analysis to provide recommendations for additional activity, and or improvements in physical health. The process therefore continues where data is captured, analyzed, synchronized, and recommendations are produced. In some embodiments, the captured data can be itemized and partitioned based on the type of activity being performed, and such information can be provided to the user on the website via graphical user interfaces, or by way of the application executed on the user's smart phone (by way of graphical user interfaces).

In an embodiment, the sensor or sensors of a device 100 can determine or capture data to determine an amount of movement of the monitoring device over a period of time. The sensors can include, for example, an accelerometer, a magnetometer, a gyroscope, or combinations thereof. Broadly speaking, these sensors are inertial sensors, which capture some movement data, in response to the device 100 being moved. The amount of movement (e.g., motion sensed) may occur when the user is performing an activity of climbing stairs over the time period, walking, running, etc. The monitoring device may be worn on a wrist, carried by a user, worn on clothing (using a clip, or placed in a pocket), attached to a leg or foot, attached to the user's chest, waist, or integrated in an article of clothing such as a shirt, hat, pants, blouse, glasses, and the like. These examples are not limiting to all the possible ways the sensors of the device can be associated with a user or thing being monitored.

In other embodiments, a biological sensor can determine any number of physiological characteristics of a user. As another example, the biological sensor may determine heart rate, a hydration level, body fat, bone density, fingerprint data, sweat rate, and/or a bioimpedance of the user. Examples of the biological sensors include, without limitation, a biometric sensor, a physiological parameter sensor, a pedometer, or a combination thereof In some embodiments, data associated with the user's activity can be monitored by the applications on the server and the users device, and activity associated with the user's friends, acquaintances, or social network peers can also be shared, based on the user's authorization. This provides for the ability for friends to compete regarding their fitness, achieve goals, receive badges for achieving goals, get reminders for achieving such goals, rewards or discounts for achieving certain goals, etc.

As noted, an activity tracking device 100 can communicate with a computing device (e.g., a smartphone, a tablet computer, a desktop computer, or computer device having wireless communication access and/or access to the Internet). The computing device, in turn, can communicate over a network, such as the Internet or an Intranet to provide data synchronization. The network may be a wide area network, a local area network, or a combination thereof The network may be coupled to one or more servers, one or more virtual machines, or a combination thereof. A server, a virtual machine, a controller of a monitoring device, or a controller of a computing device is sometimes referred to herein as a computing resource. Examples of a controller include a processor and a memory device.

In one embodiment, the processor may be a general purpose processor. In another embodiment, the processor can be a customized processor configured to run specific algorithms or operations. Such processors can include digital signal processors (DSPs), which are designed to execute or interact with specific chips, signals, wires, and perform certain algorithms, processes, state diagrams, feedback, detection, execution, or the like. In some embodiments, a processor can include or be interfaced with an application specific integrated circuit (ASIC), a programmable logic device (PLD), a central processing unit (CPU), or a combination thereof, etc.

In some embodiments, one or more chips, modules, devices, or logic can be defined to execute instructions or logic, which collectively can be viewed or characterized to be a processor. Therefore, it should be understood that a processor does not necessarily have to be one single chip or module, but can be defined from a collection of electronic or connecting components, logic, firmware, code, and combinations thereof Examples of a memory device include a random access memory (RAM) and a read-only memory (ROM). A memory device may be a Flash memory, a redundant array of disks (RAID), a hard disk, or a combination thereof Embodiments described in the present disclosure may be practiced with various computer system configurations including hand-held devices, microprocessor systems, microprocessor-based or programmable consumer electronics, minicomputers, mainframe computers and the like. Several embodiments described in the present disclosure can also be practiced in distributed computing environments where tasks are performed by remote processing devices that are linked through a wire-based or wireless network.

With the above embodiments in mind, it should be understood that a number of embodiments described in the present disclosure can employ various computer-implemented operations involving data stored in computer systems. These operations are those requiring physical manipulation of physical quantities. Any of the operations described herein that form part of various embodiments described in the present disclosure are useful machine operations. Several embodiments described in the present disclosure also relate to a device or an apparatus for performing these operations. The apparatus can be specially constructed for a purpose, or the apparatus can be a computer selectively activated or configured by a computer program stored in the computer. In particular, various machines can be used with computer programs written in accordance with the teachings herein, or it may be more convenient to construct a more specialized apparatus to perform the required operations.

Various embodiments described in the present disclosure can also be embodied as computer-readable code on a non-transitory computer-readable medium. The computer-readable medium is any data storage device that can store data, which can thereafter be read by a computer system. Examples of the computer-readable medium include hard drives, network attached storage (NAS), ROM, RAM, compact disc-ROMs (CD-ROMs), CD-recordables (CD-Rs), CD-rewritables (RWs), magnetic tapes and other optical and non-optical data storage devices. The computer-readable medium can include computer-readable tangible medium distributed over a network-coupled computer system so that the computer-readable code is stored and executed in a distributed fashion.

Although the method operations were described in a specific order, it should be understood that other housekeeping operations may be performed in between operations, or operations may be performed in an order other than that shown, or operations may be adjusted so that they occur at slightly different times, or may be distributed in a system which allows the occurrence of the processing operations at various intervals associated with the processing.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the various embodiments described in the present disclosure are not to be limited to the details given herein, but may be modified within the scope and equivalents of the appended claims.

The invention claimed is:

1. A computer-implemented method comprising:
   obtaining motion data indicative of activity metrics for a user wearing an activity tracking device; and
   selecting one of a first data transfer rate or a second data transfer rate for communicating the motion data over a wireless network to a mobile computing device dependent upon a status of an activity tracking application installed on a mobile computing device;
   communicating the motion data over the wireless network to the mobile computing device at the selected one of the first data transfer rate or the second data transfer rate, the mobile computing device configured to display one or more of the activity metrics, wherein communicating the motion data to the mobile computing device comprises:
      communicating the motion data at the first data transfer rate when the status of the activity tracking application is that the activity tracking application is open, wherein communicating the motion data at the first data transfer rate comprising scaling a connection interval associated with the wireless network down to be within a first range of values when the activity tracking application is open, wherein the first data transfer rate comprises command data requesting data from the activity tracking device, sending motion data, and acknowledgment data from the activity tracking device; and
      communicating the motion data at the second data transfer rate when the status of the activity tracking application is that the activity tracking application is closed, wherein motion data communicated at the first data transfer rate and the motion data communicated at the second transfer rate are transmitted across the same communication channel, wherein communicating the motion data at the second data transfer rate comprises scaling the connection interval up to be within a second range of values when the activity tracking application is closed, the second range of values being different than the first range of values, wherein the second range of values is greater than the first range of values, wherein real-time updates are transferred at the second data transfer rate.

2. The computer-implemented method of claim 1, wherein:
   the first range of values spans from 10 milliseconds to 30 milliseconds; and
   the second range of values spans from 200 milliseconds to 500 milliseconds.

3. The computer-implemented method of claim 1, wherein the one or more activity metrics include a step count of the user.

4. The computer-implemented method of claim 1, wherein the one or more activity metrics include a number of floors climbed by the user.

5. The computer-implemented method of claim 1, further comprising:
   pairing the activity tracking device with the mobile computing device prior to communicating the motion data over the wireless network.

6. The computer-implemented method of claim 1, wherein the wireless network includes a local area network.

7. The computer-implemented method of claim 1, wherein the mobile computing device is a smartphone.

8. The computer-implemented method of claim 1, wherein background updates are enabled when the activity tracking application is closed and at an instance where the activity tracking device indicates it has data to sync.

9. An activity tracking device comprising:
   one or more motion sensors; and
   one or more computing devices communicatively coupled with the one or more motion sensors, the one or more computing devices configured to perform operations, the operations comprising:
      obtaining, via the one or more motions sensors, motion data indicative of activity metrics for a user wearing the activity tracking device; and
      selecting one of a first data transfer rate or a second data transfer rate for communicating the motion data over a wireless network to a mobile computing device dependent upon a status of an activity tracking application installed on the mobile computing device
      communicating the motion data over the wireless network to the mobile computing device at the selected one of the first data transfer rate or the second data transfer rate, the mobile computing device configured to display one or more of the activity metrics, wherein communicating the motion data to the mobile computing device comprises:
         communicating the motion data at the first data transfer rate when the status of the activity tracking application is that the activity tracking application is open, wherein communicating the motion data at the first data transfer rate comprises scaling a connection interval associated with the wireless network down to be within a first range of values when the activity tracking application is open, wherein the first data transfer rate comprises command data requesting data from the activity tracking device, sending the motion data, and acknowledgment data from the activity tracking device; and communicating the motion data at the second data transfer rate when the status of the activity tracking application is that the activity tracking application is closed, wherein the motion data communicated at the first data transfer rate and the motion data communicated at the second transfer rate are transmitted across the same communication channel, wherein communicating the motion data at the second data transfer rate comprising scaling the connection interval up to be within a second range of values when the activity tracking application is closed, the second range of values being different than the first range of values, wherein the second range of values is greater than the first range of values, wherein real-time updates and transferred at the second data transfer rate.

10. The activity tracking device of claim 9, wherein the one or more activity metrics include a step count of the user.

11. The activity tracking device of claim 9, wherein the operations further include:

pairing the activity tracking device with the mobile computing device prior to communicating the motion data over the wireless network.

12. The computer-implemented method of claim 8, wherein the background update occurs at the first data transfer rate.

* * * * *